US008092495B2

(12) United States Patent
Boulis et al.

(10) Patent No.: US 8,092,495 B2
(45) Date of Patent: Jan. 10, 2012

(54) SPINAL PLATFORM AND METHOD FOR DELIVERING A THERAPEUTIC AGENT TO A SPINAL CORD TARGET

(75) Inventors: Nicholas M. Boulis, DeCatur, GA (US); Anthony J. Shawan, Brecksville, OH (US); Helmuth Kotschi, Middleburg Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 141 days.

(21) Appl. No.: 12/418,170

(22) Filed: Apr. 3, 2009

(65) Prior Publication Data

US 2010/0030184 A1 Feb. 4, 2010

Related U.S. Application Data

(60) Provisional application No. 61/042,307, filed on Apr. 4, 2008, provisional application No. 61/082,787, filed on Jul. 22, 2008.

(51) Int. Cl.
*A61B 17/70* (2006.01)

(52) U.S. Cl. ........... 606/246; 604/116; 604/512; 606/92

(58) Field of Classification Search .................. 604/116, 604/174, 512; 606/92–94, 246–250
See application file for complete search history.

(56) References Cited

U.S. PATENT DOCUMENTS

| 5,871,487 A | 2/1999 | Warner et al. |
| 7,107,091 B2 | 9/2006 | Jutras et al. |
| 2003/0187351 A1 | 10/2003 | Franck et al. |
| 2008/0154262 A1 | 6/2008 | Brundobler et al. |
| 2008/0306518 A1 | 12/2008 | Cain et al. |
| 2009/0192487 A1* | 7/2009 | Broaddus et al. ............. 604/506 |

FOREIGN PATENT DOCUMENTS

DE 202006019649 U1 9/2007

OTHER PUBLICATIONS

Riley et al., "Cervical Spinal Cord Therapeutics Delivery: Preclinical Safety Validation of a Tabilized Microinjection Platform", *Neurosurgery*, reprinted from www.neurosurgery-online.com on Mar. 30, 2009, pp. 1-8.
Riley et al., "Targeted Spinal Cord Therapeutics Delivery: Stabilized Platform and Microelectrode Recording Guidance Validation", *Stereotact Funct Neurosurg* 151, Aug. 11, 2007, pp. 1-8.

* cited by examiner

*Primary Examiner* — Kevin C Sirmons
*Assistant Examiner* — Emily Schmidt
(74) *Attorney, Agent, or Firm* — Tarolli, Sundheim, Covell & Tummino LLP

(57) ABSTRACT

A spinal platform for delivering a therapeutic agent to a spinal cord target includes a brace member for attachment to a plurality of bony structures surrounding at least a portion of the spinal cord target, a carriage member operatively coupled to and movable along the brace member, and a universal joint for adjusting the coronal or sagittal angle of a surgical instrument. The brace member includes at least one longitudinal rail and a plurality of attachment members. The plurality of attachment members is operably connected to the at least one longitudinal rail. The at least one longitudinal rail includes a proximal end portion, a distal end portion, and a middle portion extending between the proximal and distal end portions. The universal joint is seated within a portion of the carriage member and is capable of delivering the therapeutic agent to the spinal cord target.

15 Claims, 31 Drawing Sheets

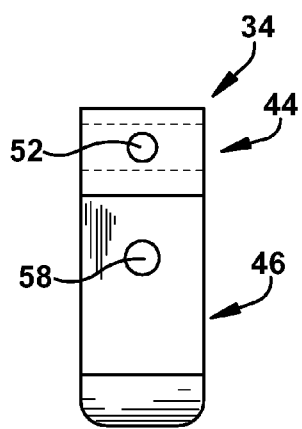
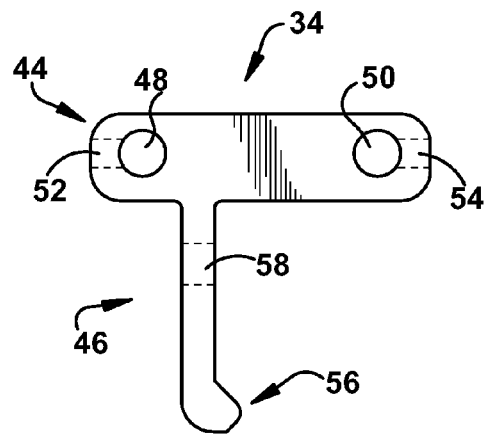
Fig. 3A    Fig. 3B
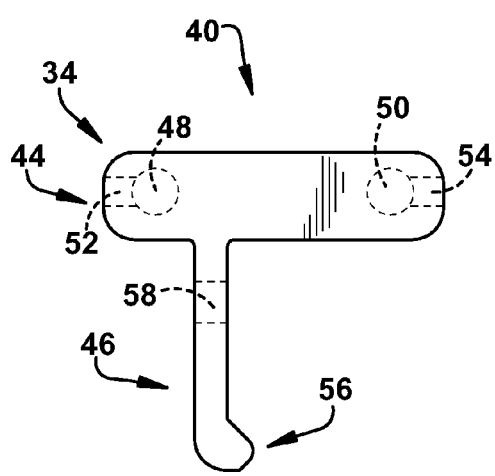
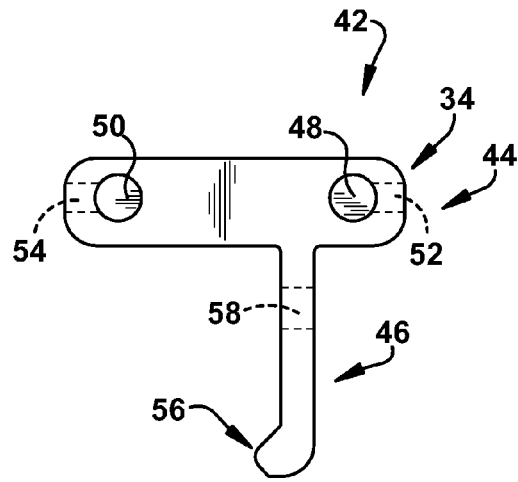
Fig. 3C    Fig. 3D
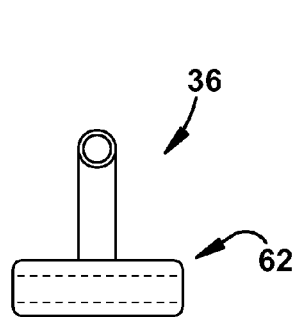
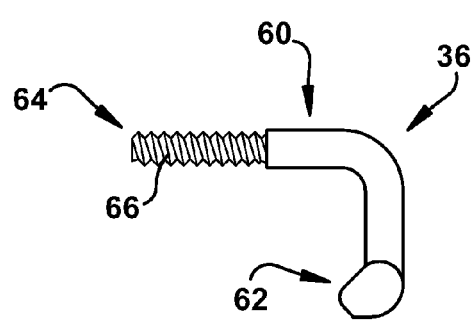
Fig. 3E    Fig. 3F

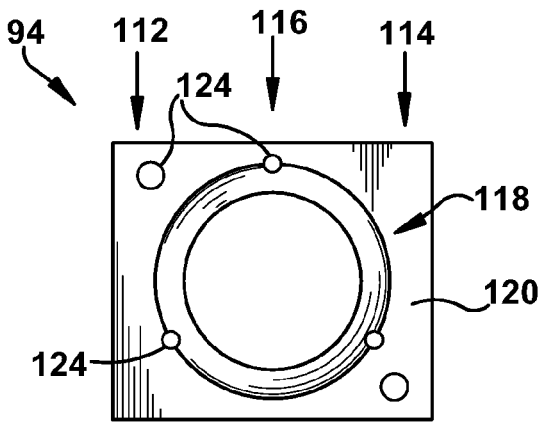
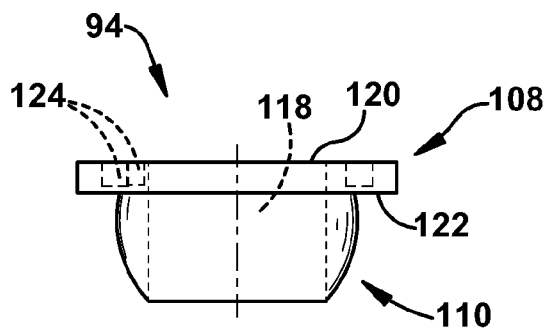
Fig. 5A
Fig. 5B
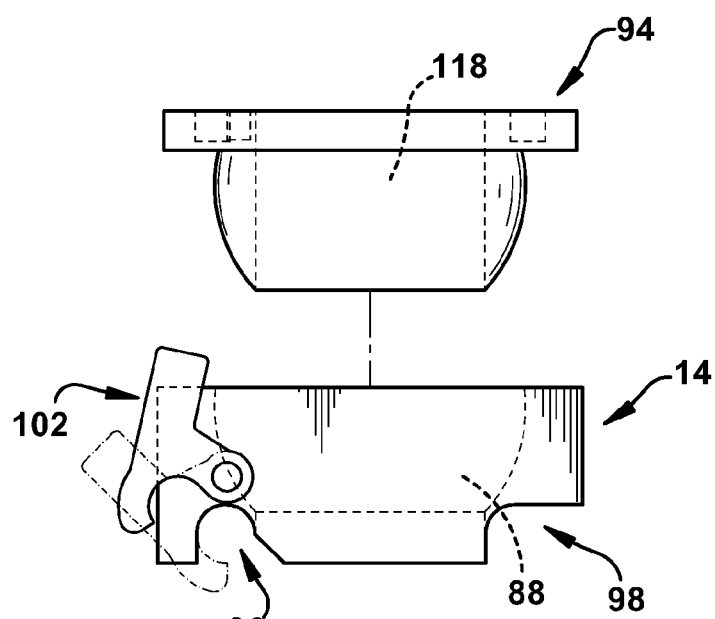
Fig. 5C
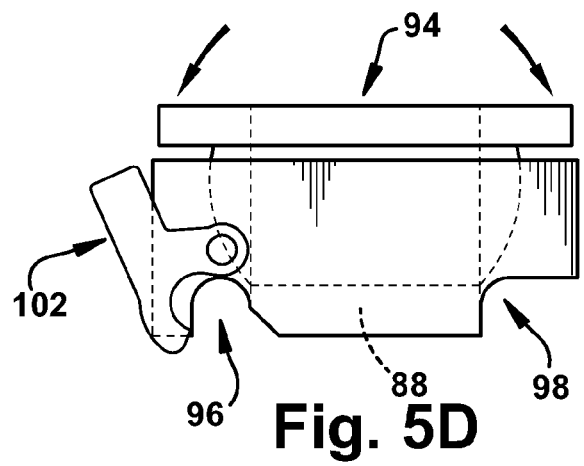
Fig. 5D

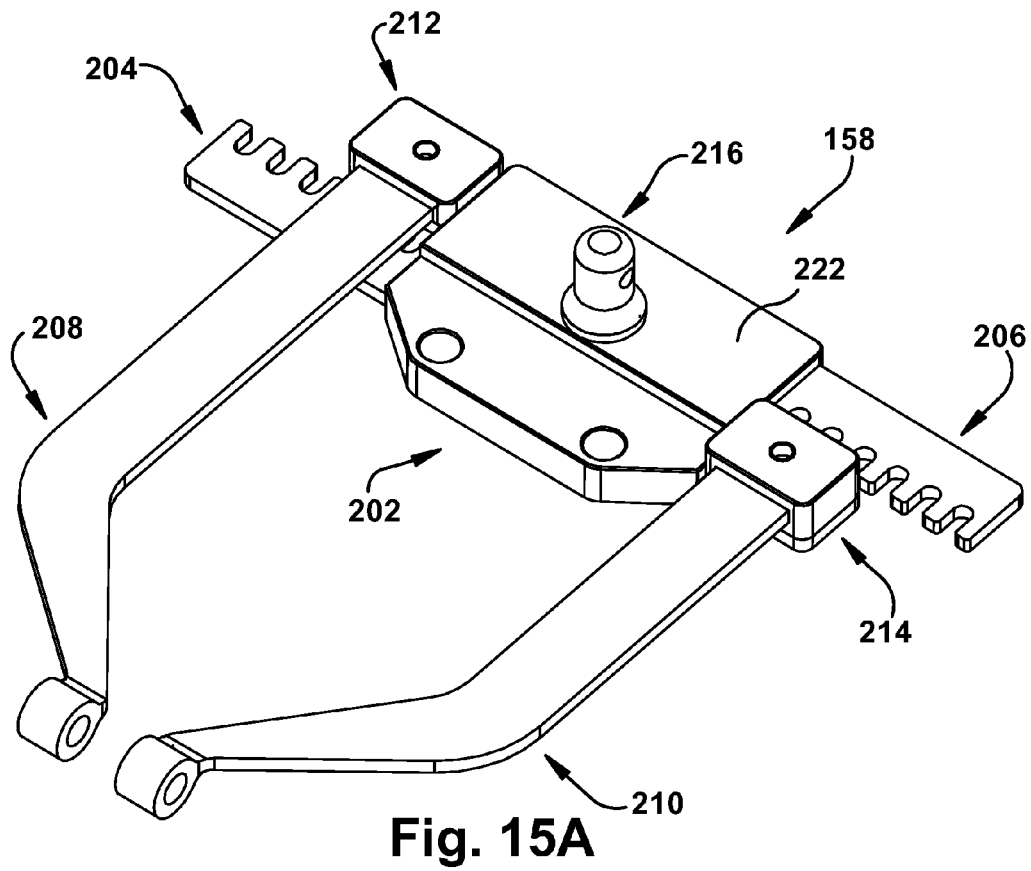
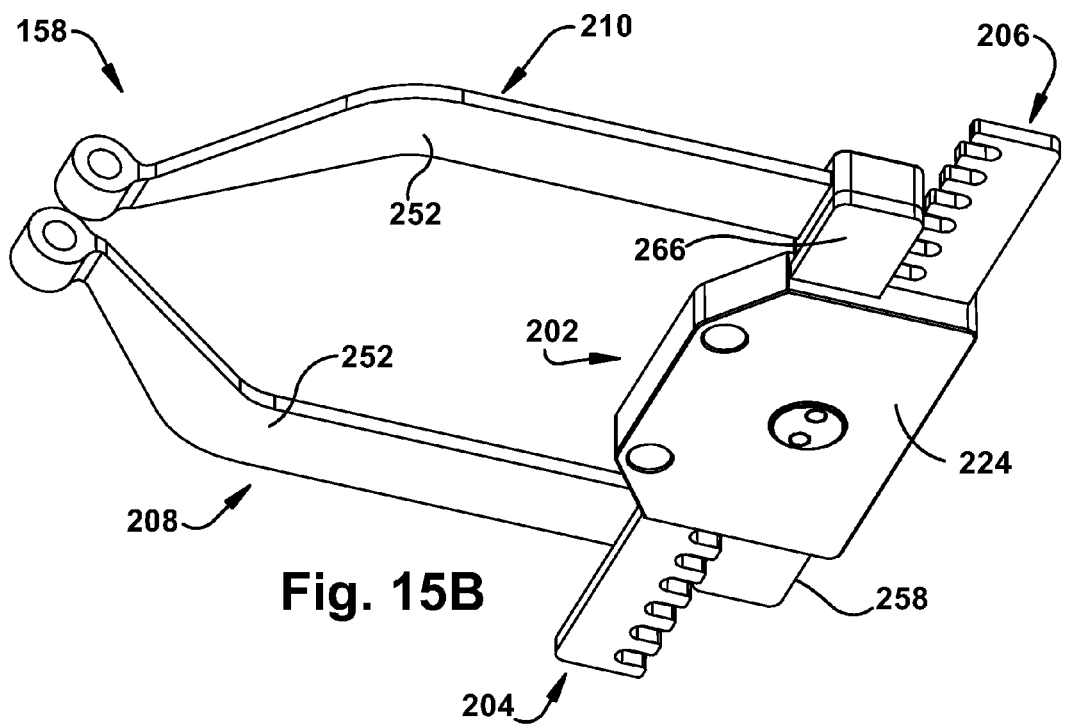

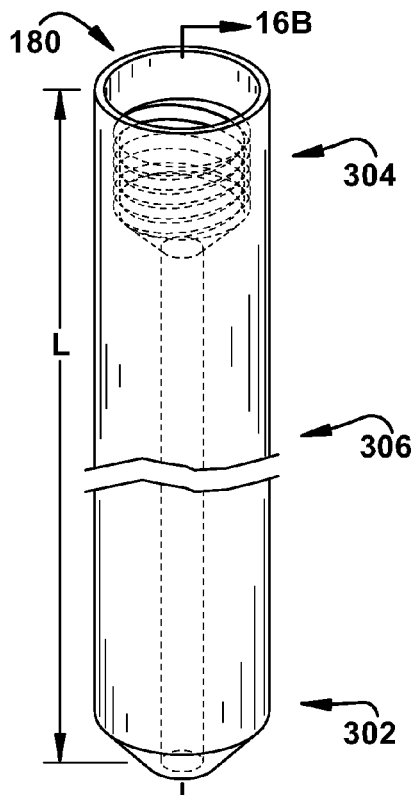
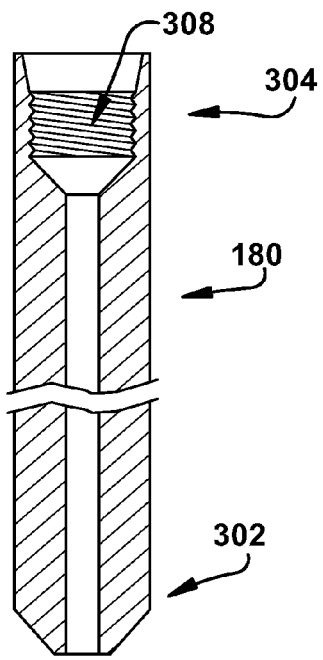
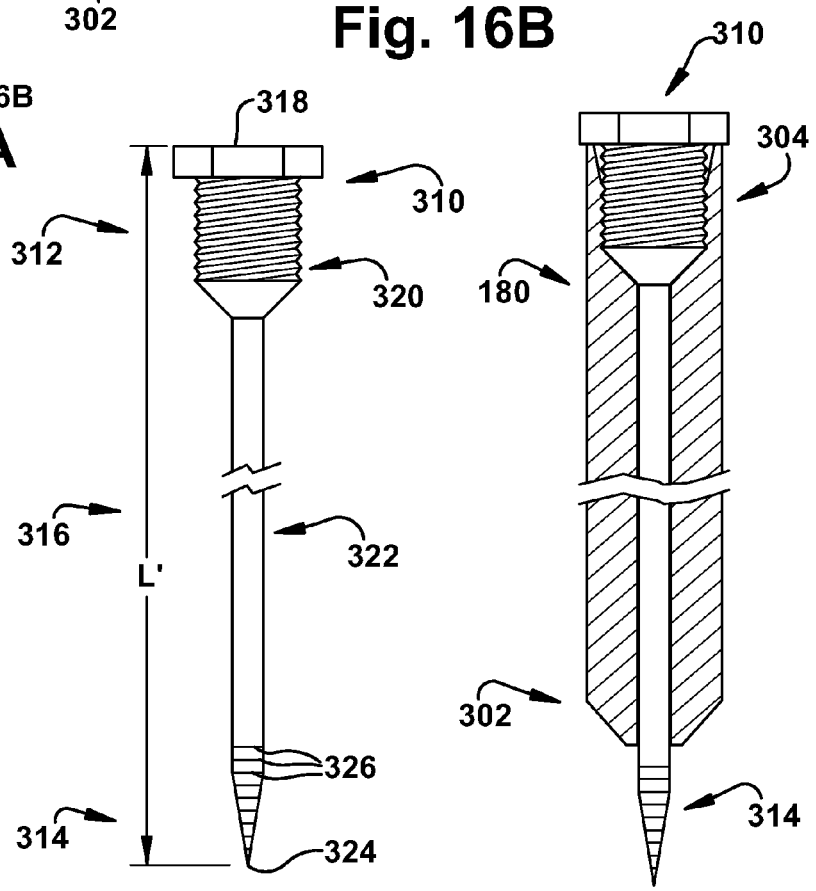
Fig. 16A
Fig. 16B
Fig. 16C
Fig. 16D

SPINAL PLATFORM AND METHOD FOR DELIVERING A THERAPEUTIC AGENT TO A SPINAL CORD TARGET

RELATED APPLICATIONS

This application claims priority to U.S. Provisional Patent Application Ser. No. 61/042,307, filed Apr. 4, 2008, and U.S. Provisional Patent Application Ser. No. 61/082,787, filed Jul. 22, 2008, the entireties of which are hereby incorporated by reference.

TECHNICAL FIELD

The present invention relates generally to an apparatus and method for stabilizing instrument guidance during spinal surgery, and more particularly to a spinal platform and related method for stabilized delivery of a therapeutic agent to a spinal cord target.

BACKGROUND OF THE INVENTION

The delivery of cellular and molecular therapies to the spinal cord holds significant promise for the treatment of traumatic, autoimmune, degenerative and functional spinal cord diseases, all of which are thought to result from compromised neuronal connectivity due to a combination of axonal disruption and cell body death. In an attempt to address pathogenic mechanisms underlying these conditions, therapeutic strategies have been proposed that promote neuroprotection, axonal regeneration, and/or cell-based neurorestoration through replacement of lost neural tissue or supporting stroma.

A variety of in vitro and small animal in vivo experiments demonstrate motor neuron protection and axonal regeneration through the delivery of genes for trophic factors (e.g., IGF-1, GDNF), antiapoptotic proteins (e.g., XIAP, Bcl-xL), or siRNA capable of inactivating toxic gene products (e.g., SOD1 siRNA). Vectors designed for the delivery of these genes can be injected directly into the spinal cord (in vivo gene transfer) or delivered to cells which are subsequently transplanted into the spinal cord (ex vivo gene transfer).

Some form of guidance is needed to improve localization of the therapy to the tract or neurons of interest and to reduce the incidence of off-target sequelae. Stabilization has the dual function of increasing targeting precision while also reducing sequelae as the spinal cord can remain cannulated for a period of several minutes during targeting and the infusion process. Recent successes in cell-based therapy experimentation and the proprietary development of viral vectors designed for direct parenchymal injection require a technology capable of targeted, localized administration of a biologic payload to the spinal cord.

SUMMARY OF THE INVENTION

According to one aspect of the present invention a spinal platform for delivering a therapeutic agent to a spinal cord target comprises a brace member for attachment to a plurality of bony structures surrounding at least a portion of the spinal cord target, a carriage member operatively coupled to and movable along the brace member, and a universal joint for adjusting the coronal or sagittal angle of a surgical instrument. The brace member comprises at least one longitudinal rail and a plurality of attachment members for securing the brace member to the plurality of bony structures. The plurality of attachment members is operably connected to the at least one longitudinal rail. The at least one longitudinal rail includes a proximal end portion, a distal end portion, and a middle portion extending between the proximal and distal end portions. The universal joint is seated within a portion of the carriage member and is capable of delivering the therapeutic agent to the spinal cord target.

According to another aspect of the present invention, a method is provided for delivering a therapeutic agent to a spinal cord target. One step of the method includes providing a spinal platform. The spinal platform comprises a brace member for attachment to a plurality of bony structures surrounding at least a portion of the spinal cord target, a carriage member operatively coupled to and movable along the brace member, and a universal joint seated within a portion of the carriage member. The brace member comprises at least one longitudinal rail and a plurality of attachment members operably connected to the at least one longitudinal rail. After providing the surgical platform, the plurality of attachment members is attached to first and second bony structures that surround at least a portion of the spinal cord target so that the carriage member is positioned substantially adjacent the spinal cord target. The universal joint is then manipulated to adjust the coronal or sagittal angle of the surgical instrument. The therapeutic agent is delivered to the spinal cord target via the surgical instrument.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 3A is a side view of clamp body constructed in accordance with the present invention;

FIG. 3B is a front view of the clamp body in FIG. 3A;

FIG. 3C is a front view of the brace member taken along Line 3C in FIG. 2A;

FIG. 3D is a front view of the brace member taken along Line 3D in FIG. 2A;

FIG. 3E is a front view of a clamp pin constructed in accordance with the present invention;

FIG. 3F is a side view of the clamp pin in FIG. 3E;

FIG. 5A is a top view of a universal joint constructed in accordance with the present invention;

FIG. 5B is a side view of the universal joint in FIG. 5A;

FIG. 5C is a side view of the universal joint being mated with the carriage member in FIG. 4A;

FIG. 5D is a side view showing the universal joint mated with the carriage member in FIG. 5C;

FIG. 15A is a perspective view showing the top side of a tissue retracting member;

FIG. 15B is a perspective view showing the bottom side of the tissue retracting member in FIG. 15A;

FIG. 16A is a perspective view of a percutaneous post used to affix the brace member (FIGS. 14A-B) and the tissue retracting member (FIGS. 15A-E) to a plurality of bony structures surrounding the spinal cord target;

FIG. 16B is a cross-sectional view taken along Line 16B-16B in FIG. 16A;

FIG. 16C is a side view of a self-tapping screw for insertion into the percutaneous post in FIGS. 16A-B;

FIG. 16D is a cross-sectional view showing the self-tapping screw in FIG. 16C mated with the percutaneous post in FIG. 16B;

DETAILED DESCRIPTION

Figure 1A:
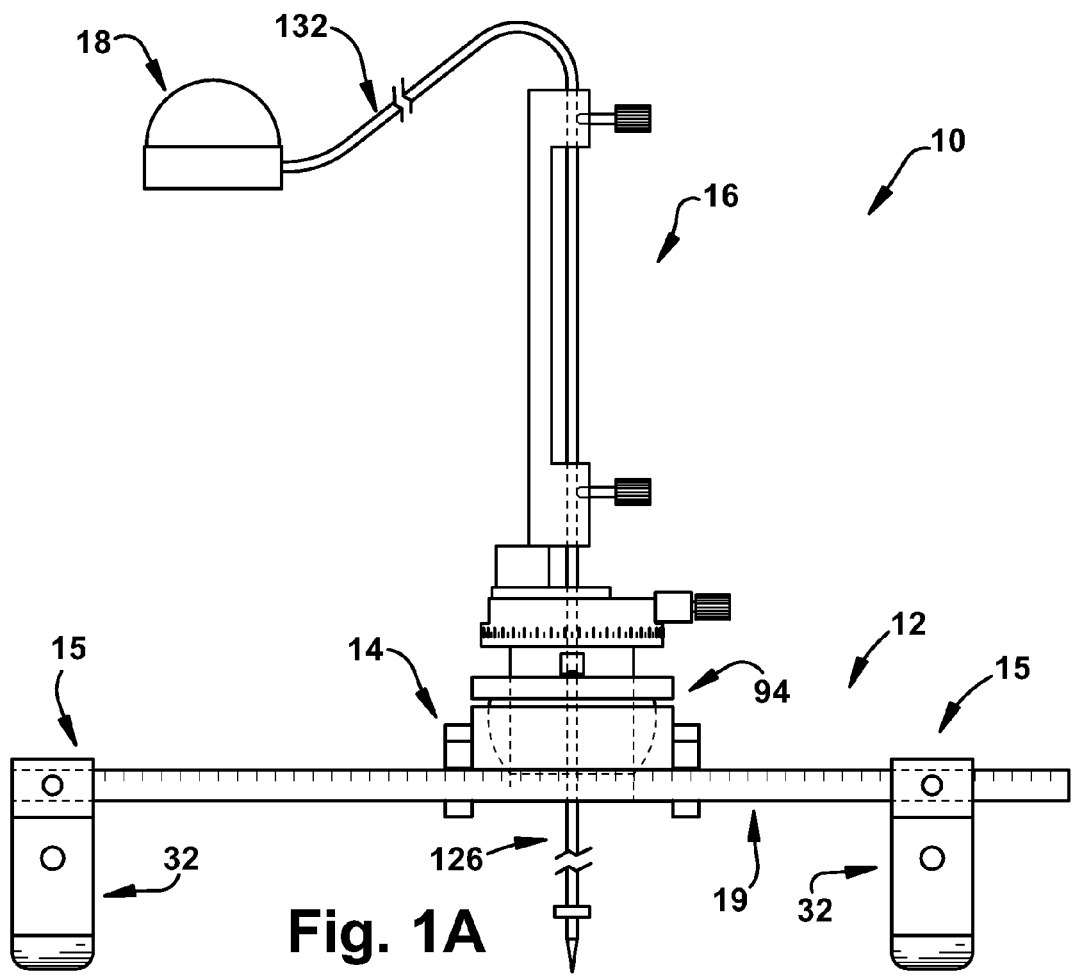
FIG. 1A is a side view of a spinal platform for delivering a therapeutic agent to a spinal cord target constructed in accordance with one aspect of the present invention.

The present invention relates generally to an apparatus and method for stabilizing instrument guidance during spinal surgery, and more particularly to a spinal platform and related method for stabilized delivery of a therapeutic agent to a spinal cord target. As representative of the present invention, FIGS. 1A-B, FIGS. 7A-B, and FIG. 13 illustrate a spinal platform 10, $10_a$, and $10_b$ for controlled and precise delivery of a therapeutic agent to a spinal cord target. The spinal platform 10, $10_a$, and $10_b$ comprises a brace member 12 and $12_b$, a carriage member 14 and $14_b$ operatively coupled to and movable along the brace member, and a universal joint 94 and $94_b$ for adjusting the coronal or sagittal angle of a surgical instrument 126. As described in more detail below, the brace member 12 and $12_b$ comprises at least one longitudinal rail 19 and a plurality of attachment members 15 for securing the brace member to a plurality of bony structures surrounding the spinal cord target. The plurality of attachment members 15 is operably connected to the at least one longitudinal rail 19. The at least one longitudinal rail 19 includes a proximal end portion 26, a distal end portion 24, and a middle portion 28 extending between the proximal and distal end portions. As also described in more detail below, the universal joint 94 and $94_b$ is seated within a portion of the carriage member 14 and $14_b$.

FIGS. 1A-8B illustrate one aspect of the present invention. As shown in FIGS. 1A-B, a spinal platform 10 for delivering a therapeutic agent to a spinal cord target can comprise a brace member 12 for attachment to a plurality of bony structures surrounding at least a portion of the spinal cord target. The plurality of bony structures can comprise any portion of the vertebral column (generally shown in FIGS. 10-11) (e.g., cervical, thoracic, lumbar, sacral), as well as any portion of the cranium (generally shown in FIG. 12) (e.g., the occipital bone or occiput). Unlike spinal platforms of the prior art, the lightweight construction of the spinal platform 10 permits attachment of the spinal platform 10 to a plurality of bony structures, such as the spinous processes.

Figure 2A:
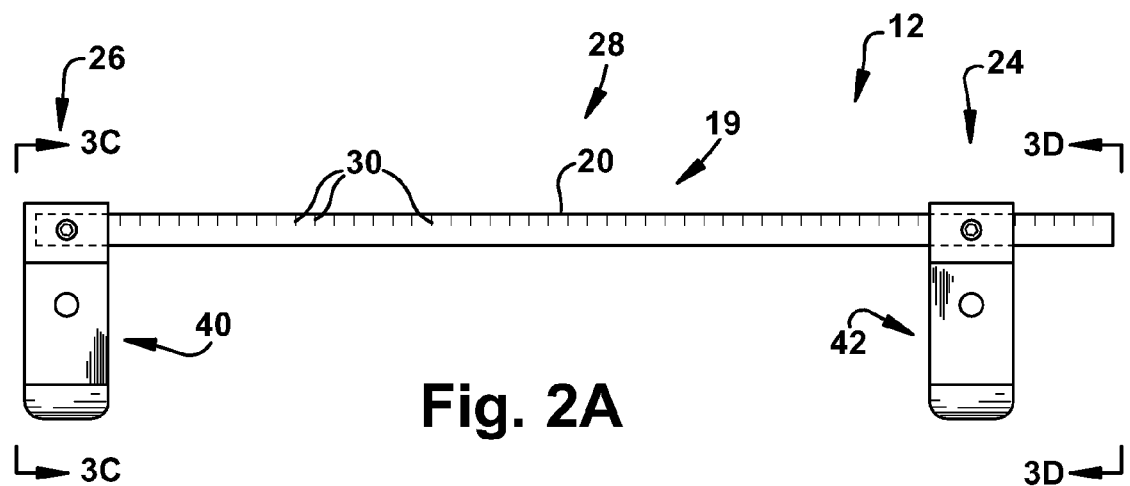
FIG. 2A is a side view of a brace member constructed in accordance with the present invention.
Figure 2B:
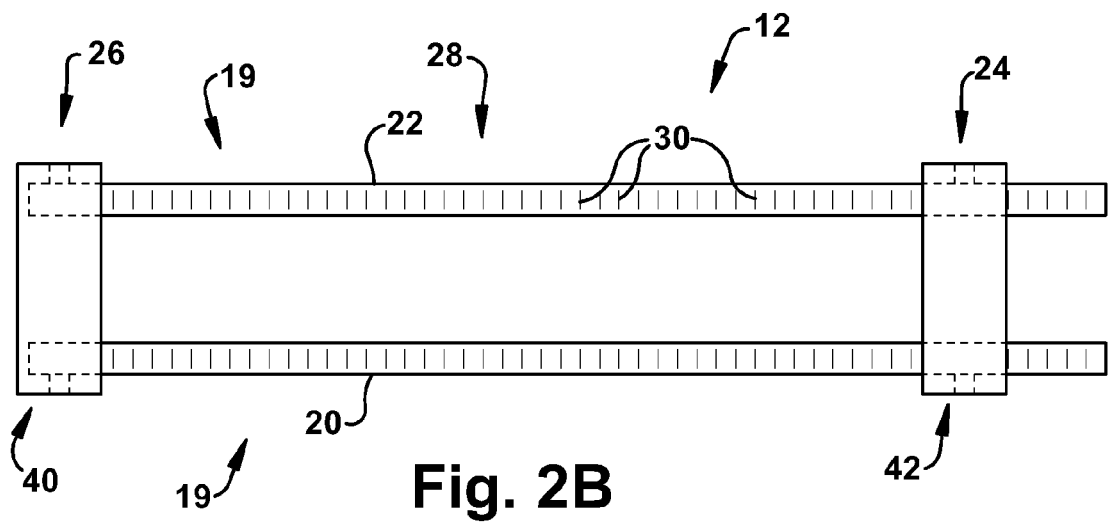
FIG. 2B is a top view of the brace member in FIG. 2A.

The brace member 12 (FIGS. 2A-B) can comprise at least one longitudinal rail 19. As shown in FIGS. 2A-B, for example, the brace member 12 can include oppositely disposed first and second longitudinal rails 20 and 22. It will be appreciated that any number of longitudinal rails 19 can form the brace member 12. The length of the first and second longitudinal rails 20 and 22 can be varied depending on a variety of factors, including the anatomy of the bony structure(s) and the location of the spinal cord target. The first and second longitudinal rails 20 and 22 can have approximately the same length and include a plurality of score marks 30 for measuring the distance between spinal cord target sites. The first and second longitudinal rails 20 and 22 can have a solid or semi-solid construction, and can be made of any one or combination of medical grade materials, such as stainless steel, titanium, or other known metal alloy.

Figure 3G:
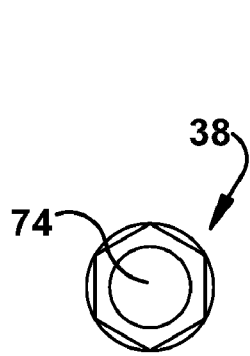
FIG. 3G is a front view of a clamp fastener constructed in accordance with the present invention.
Figure 3H:
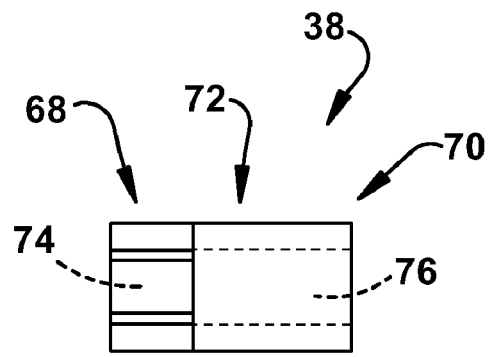
FIG. 3H is a side view of the clamp fastener in FIG. 3G.
Figure 3I:
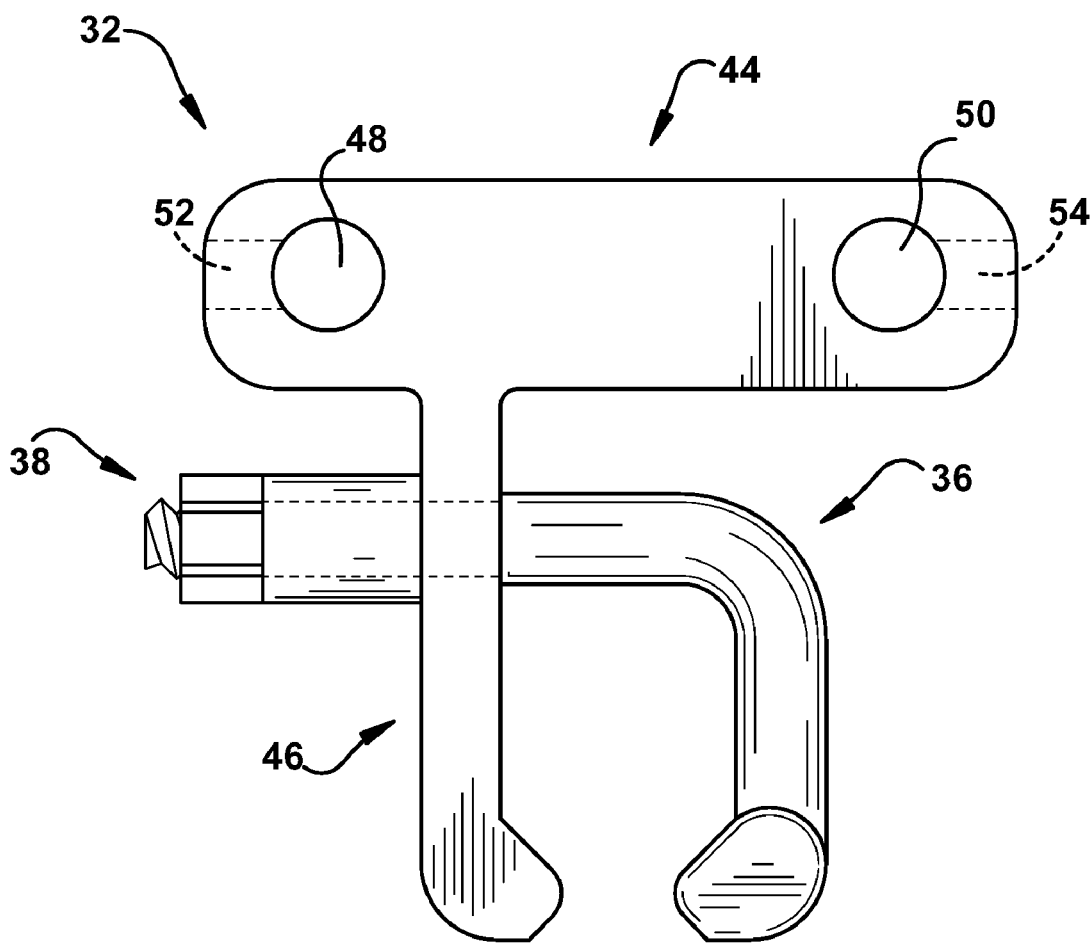
FIG. 3I is a front view of a clamp member in an assembled configuration.

A plurality of attachment members 15 are operably connected to and extend between the first and second longitudinal rails 20 and 22. One configuration of the attachment members 15 is illustrated in FIGS. 3A-I. In FIGS. 3A-I, the attachment members 15 can comprise a plurality of clamp members 32 operably attached to the first and second longitudinal rails 20 and 22. The clamp members 32 can facilitate attachment of the brace member 12 to the plurality of bony structure. The clamp members 32 (FIG. 3E) can include a clamp body 34 (FIGS. 3A-D), a clamp pin 36 (FIGS. 3E-F), and a clamp fastener 38 (FIGS. 3G-H). As shown in FIGS. 2A-B, a first clamp member 40 can be operably attached to the proximal end portion 26 of each of the first and second longitudinal rails 20 and 22. Additionally, a second clamp member 42 can be operably attached to the distal end portion 24 of each of the first and second longitudinal rails 20 and 22. It will be appreciated that one, three, four, or even more clamp members 32 can be included as part of the brace member 12. The clamp members 32 can be made of any one or combination of medical grade materials, such as stainless steel, titanium, or other known metal alloy, or rigid MRI-compatible material to facilitate application of real-time MRI targeting of the spinal cord target.

As shown in FIGS. 3A-B, each of the first and second clamp members 40 and 42 can include a T-shaped clamp body 34. The clamp body 34 can include a receptacle portion 44 for receiving the first and second longitudinal rails 20 and 22, and an arm portion 46 for contacting the bony structure(s). The receptacle portion 44 can have a flattened, rectangular shape and includes first and second openings 48 and 50 for receiving the first and second longitudinal rails 20 and 22, respectively. As shown in FIG. 3C, the first and second openings 48 and 50 of the first clamp member can form cavities into which the proximal end portion 26 of each of the first and second longitudinal rails 20 and 22 are snugly received (respectively). The first and second openings 48 and 50 of the second clamp member 42 can form channels through which the first and second longitudinal rails 20 and 22 may extend (FIG. 3D), respectfully. The receptacle portion 44 can also include first and second channels 52 and 54 that extend axial to the first and second openings 48 and 50. The first and second channels 52 and 54 are capable of receiving a screw or pin (not shown) to secure the first and second longitudinal rails 20 and 22 in the first and second openings 48 and 50 of the receptacle portion 44.

The arm portion 46 of the first and second clamp members 40 and 42 can extend substantially perpendicular to the receptacle portion 44 and include a C-shaped end 56 for contacting a bony structure, such as a spinous process. The arm portion 46 can also include a channel 58 for receiving the clamp pin 36 (FIGS. 3E-F). The dimensions of the arm portion 46 can be adjusted based on the anatomy of a subject and/or the location of the spinal cord target.

Referring to FIGS. 3E-F, the clamp pin 36 can have an L-shaped configuration and include a transverse arm portion 60 integrally formed with a bean-shaped contacting portion 62. The transverse arm portion 60 can include a first end 64 for extending through the channel 58 of the arm portion 46. The first end 64 can also includes a cavity 66 for receiving a tightening tool (not shown) to adjust the position of the clamp pin 36 relative to the arm portion 46 of the clamp body 34. The contacting portion 62 of the clamp pin 36 can be adapted for contact with a bony structure (e.g., a spinous process) opposite the C-shaped end 56 of the arm portion 46.

Each of the first and second clamp members 40 and 42 can also include a clamp fastener 38 for securing the clamp pin 36 to the clamp body 34. As shown in FIGS. 3G-H, the clamp fastener 38 can have a hollow, cylindrical shape and include a first end portion 68, a second end portion 70, and middle portion 72 extending between the first and second end portions. The first end portion 68 can include a hex-shaped receptacle 74 for receiving a tightening tool (e.g., a hex wrench) (not shown). The clamp fastener 38 can also include a channel 76 extending between the first and second end portions 68 and 70. The channel 76 can be adapted for receiving both the tightening tool and the first end 64 of the clamp pin 36. By rotating the clamp fastener 38 either clockwise or counterclockwise (i.e., with the tightening tool), the position of the clamp pin 36 relative to the arm portion 46 of the clamp body 34 can be selectively adjusted (i.e., tightened or loosened).

Figure 1B:
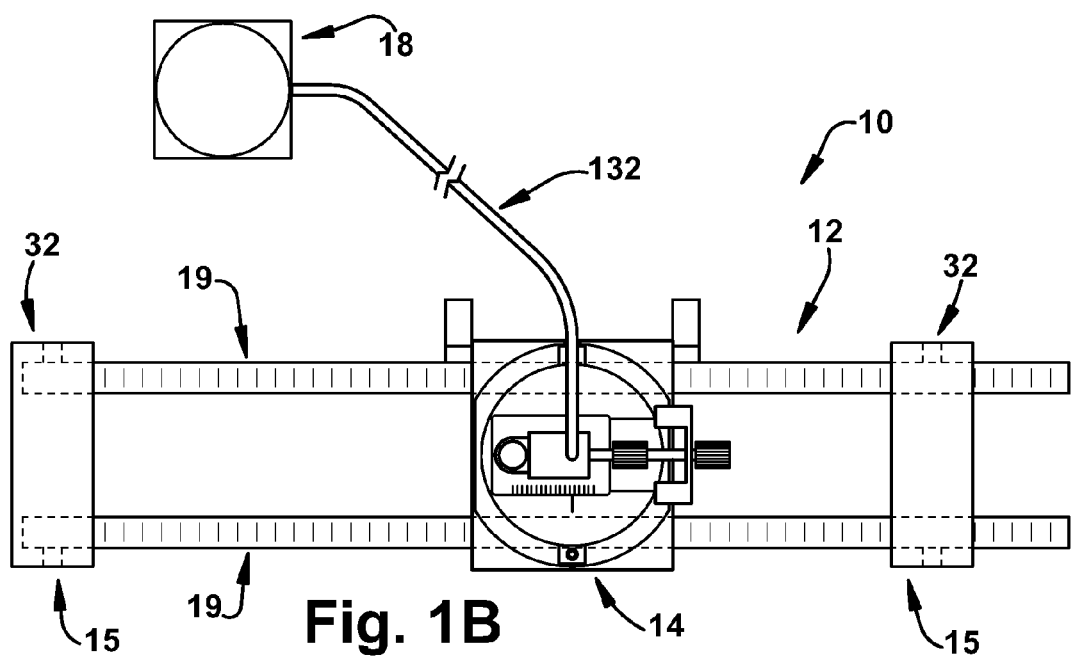
FIG. 1B is a top view of the spinal platform in FIG. 1A.
Figure 4A:
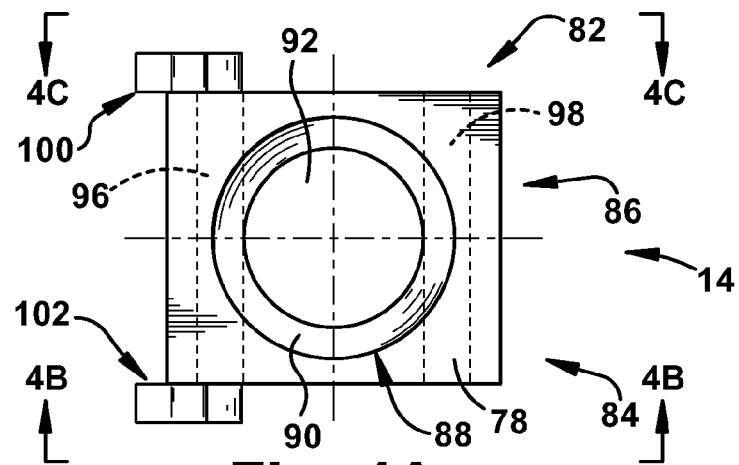
FIG. 4A is a top view of a carriage member constructed in accordance with the present invention.
Figure 4B:
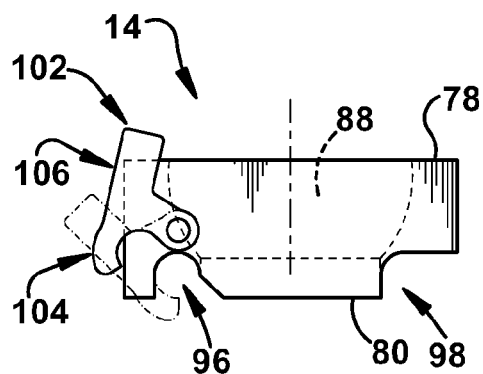
FIG. 4B is a side view of the carriage member taken along Line 4B in FIG. 4A.
Figure 4C:
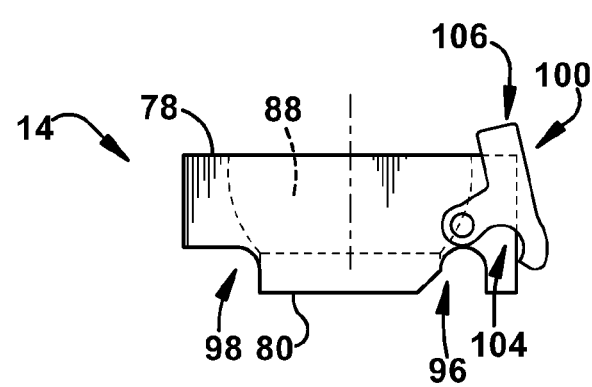
FIG. 4C is a side view of the carriage member taken along Line 4C in FIG. 4A.

The carriage member 14 can be operably mounted to and movable along the brace member 12 (FIGS. 1A-B). As shown in FIGS. 4A-C, the carriage member 14 can have a flattened, square-like main body including oppositely disposed first and second major surfaces 78 and 80. Additionally, the carriage member 14 can include a first end portion 82, a second end portion 84, and a middle portion 86 extending between the first and second end portions. The carriage member 14 can be made of any one or combination of medical grade materials, such as stainless steel, titanium, or other known metal alloy. It will be appreciated that the main body can have a shape other than the one illustrated in FIGS. 4A-C.

Figure 6A:
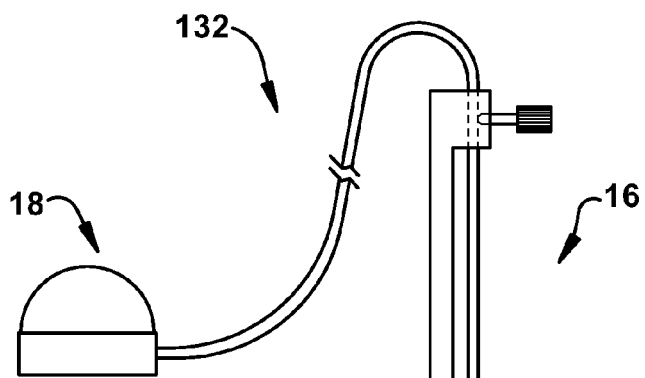
FIG. 6A is a side view of a micromanipulator and a pump operably mounted to the universal joint and carriage member in FIG. 5D.
Figure 6B:
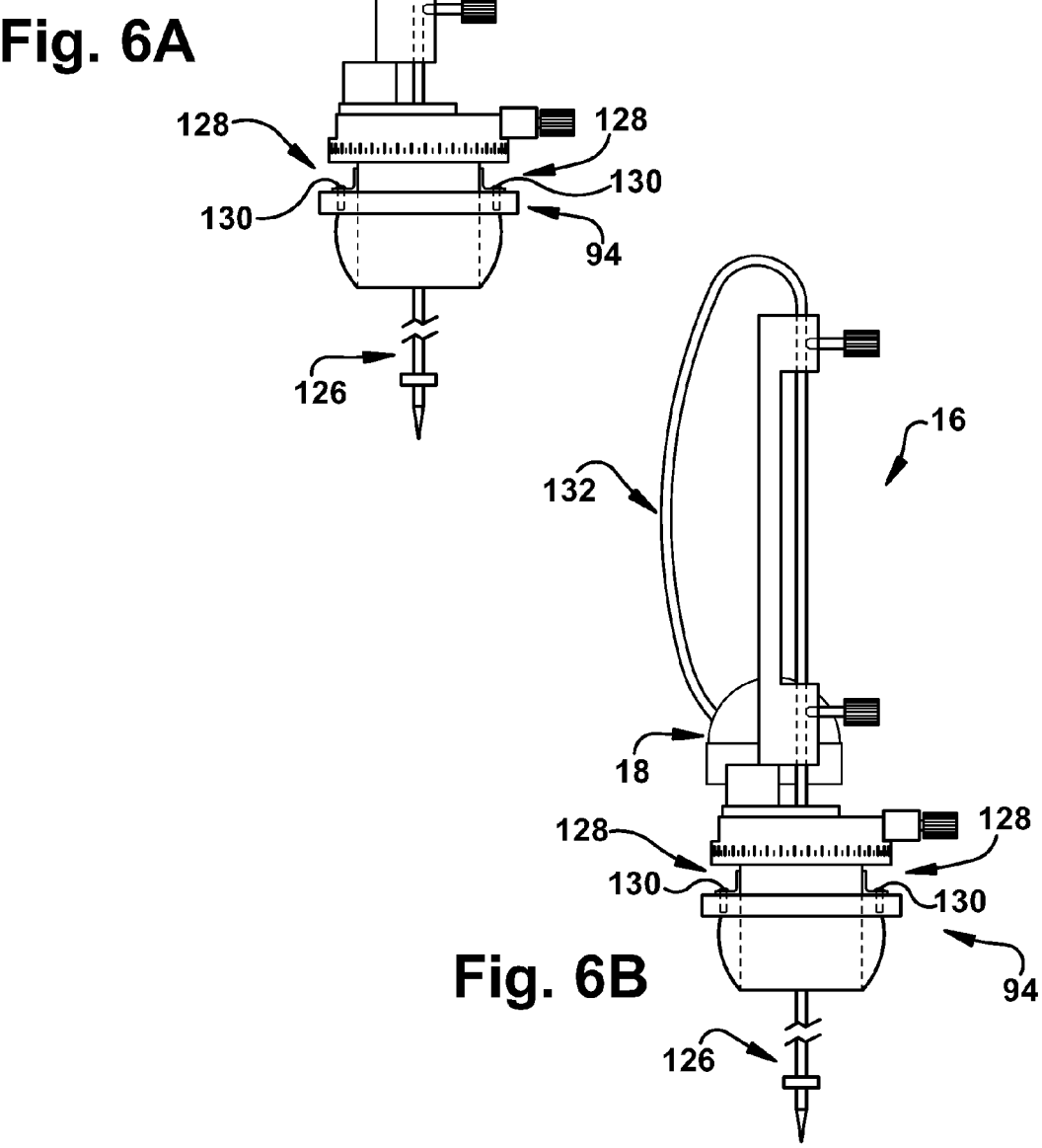
FIG. 6B is a side view showing an alternative embodiment of the micromanipulator in FIG. 6A.

As shown in FIGS. 4B-C, the carriage member 14 can include a channel 88 that extends between the first and second major surfaces 78 and 80. The channel 88 can have a bowl-shaped configuration and include a first opening 90 located at the first major surface 78 and a second opening 92 located at the second major surface 80. The diameter of the first opening 90 can be greater than the diameter of the second opening 92. As described in more detail below, the channel 88 can be adapted for receiving a universal joint 94 (FIGS. 5A-B) and a portion of a micromanipulator 16 (FIGS. 6A-B).

The second major surface 80 (FIGS. 4A-C) of the carriage member 14 can be adapted to mate with the first and second longitudinal rails 20 and 22. More particularly, the second major surface 80 can include first and second tracks 96 and 98 that extend between the first and second end portions 82 and 84 of the carriage member 14. The first and second tracks 96 and 98 can be adapted to respectively receive the first and second longitudinal rails 20 and 22. The first and second tracks 96 and 98 can permit quick and easy movement of the carriage member 14 across the brace member 12.

The carriage member 14 can also include first and second locking mechanisms 100 and 102 for securing the carriage member at a desired position along the brace member 12. As shown in FIGS. 4A-C, the first and second locking mechanisms 100 and 102 can be operably attached to the first and second end portions 82 and 84 of the carriage member, respectively. Each of the first and second locking mechanisms 100 and 102 can have a Y-shaped configuration and includes a mating portion 104 and a tensioning portion 106. The mating portion 104 can have a C-shaped configuration and is adapted for contacting a portion of the first longitudinal rail 20. The tensioning portion 106 may be integrally formed with the mating portion 104 and have a stem-like configuration to facilitate movement of the mating portion (i.e., by tactile force).

Referring to FIGS. 5A-B, the universal joint 94 can comprise a flattened, square-shaped upper platform 108 and a bowl-shaped lower portion 110. The upper platform 108 can include a first end portion 112, a second end portion 114, and a middle portion 116 extending between the first and second end portions. The universal joint 94 can also include a channel 118 that extends between the upper and lower portions 108 and 110. The channel 118 can be adapted for receiving a portion of the micromanipulator 16 (FIGS. 6A-B). The upper platform 108 (FIGS. 5A-B) can include oppositely disposed first and second major surfaces 120 and 122. A plurality of openings 124 can extend either partly or entirely between the first and second major surfaces 120 and 122. The openings 124 may be adapted to receive screws or pins (not shown). It will be appreciated that the upper platform 108 can have a shape other than the one illustrated in FIGS. 5A-B.

The lower portion 110 of the universal joint 94 can have a bowl-like configuration and be adapted to mate with the channel 88 of the carriage member 14. As shown in FIGS. 5C-D, the universal joint 94 can be placed into the channel 88 of the carriage member 14 so that the channel 118 of the universal joint and the channel of the carriage member are in fluid communication with one another. The bowl-shaped configuration of universal joint 94 and the channel 88 of the carriage member 14 permits the upper portion 108 of the universal joint to rotate (indicated by arrows) and thereby adjust the coronal or sagittal angle of a surgical instrument 126 (FIGS. 1A-B).

Referring to FIGS. 6A-B, a micromanipulator 16 can be operably coupled to the universal joint 94. As described in more detail below, the micromanipulator 16 may be adapted for guiding a surgical instrument 126 along a constrained trajectory. Generally, the micromanipulator 16 can include any device that allows precise positioning of a surgical instrument 126 in three dimensions. The micromanipulator 16 may be comprised of linear and/or rotary stages, and may be entirely mechanical in nature or operated by electric motors or hydraulics. In one example of the present invention, the micromanipulator 16 can include any one of the micromanipulators commercially available from Narishige International USA, Inc., such as an oil hydraulic micromanipulator (e.g., Narishige model MO-97).

The micromanipulator 16 can be mounted to the universal joint 94 using any suitable approach. As shown in FIGS. 6A-B, for example, a plurality of L-braces 128 can be used to securely attach the micromanipulator 16 to the upper portion 108 of the universal joint 94. The L-braces 128 can be secured using screws 130 or pins. When the micromanipulator 16 is securely mounted to the universal joint 94, the surgical instrument 126 can be operably connected to a pump 18, such as a programmable Harvard p99 pump (Harvard, Inc.). As shown in FIG. 6A, the pump 18 can be connected to the surgical instrument 126 via a fluid delivery line 132 (e.g., silastic or TEFLON tubing). Alternatively, the pump 18 can be fixedly attached to the micromanipulator 16 (FIG. 6B).

Another aspect of the present invention is illustrated in FIGS. 7A-8B. The spinal platform $10_a$ shown in FIGS. 7A-8B can be identically constructed as the spinal platform 10 shown in FIGS. 1A-6B, except as described below. In FIGS. 7A-8B, structures that are identical as structures in FIGS. 1A-6B use the same reference numbers, whereas structures that are similar but not identical carry the suffix "a".

Figure 7A:
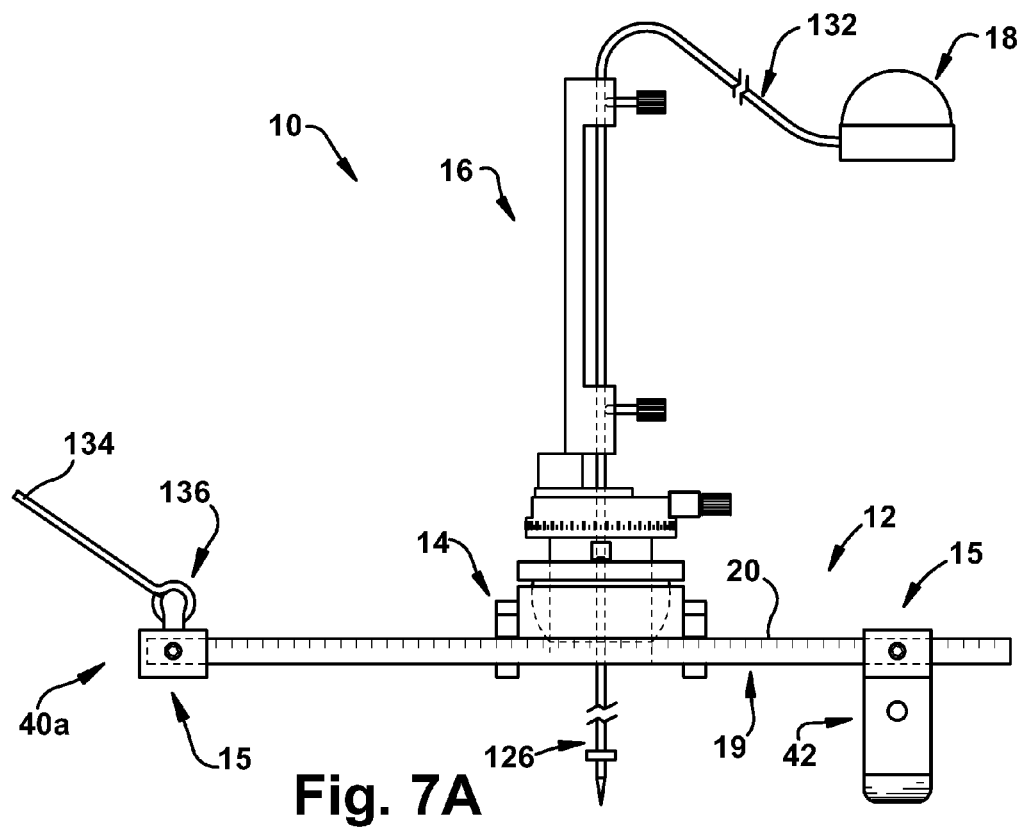
FIG. 7A is a side view showing an alternative embodiment of the spinal platform in FIG. 1A.
Figure 7B:
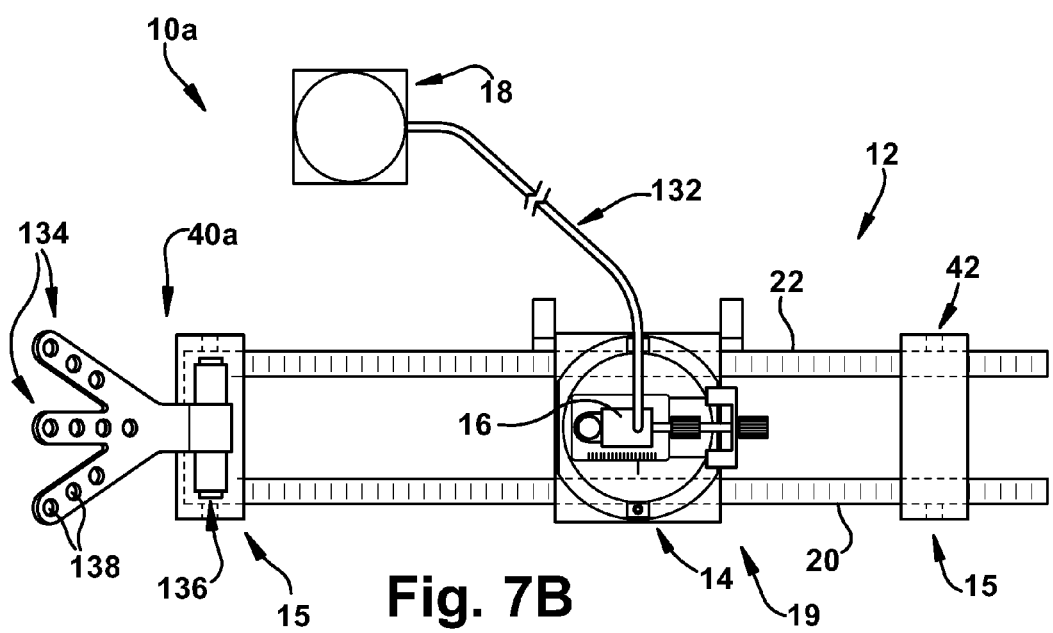
FIG. 7B is a top view of the spinal platform in FIG. 7A.

As shown in FIGS. 7A-B, the spinal platform $10_a$ can comprise a brace member 12 for attachment to a plurality of bony structures surrounding at least a portion of a spinal cord target. The brace member 12 can comprise at least one longitudinal rail 19 and a plurality of attachment members 15 attached to the at least one longitudinal rail. In FIGS. 7A-B, for example, the brace member 12 can comprise oppositely disposed first and second longitudinal rails 20 and 22, each of which can include a distal end portion 24, a proximal end portion 26, and a middle portion 28 extending between the distal and proximal end portions. It will be appreciated that the brace member 12 can include any number of longitudinal rails 19.

The plurality of attachment members 15 can include clamp members $32_a$, as described above. Additionally, the plurality of attachment members 15 can include a second clamp member 42 securely attached to the distal end portion 24 of each of the first and second longitudinal rails 20 and 22, as well as a first clamp member $40_a$ securely attached to the proximal end portion 26 of each of the first and second longitudinal rails. The first clamp member $40_a$ can comprise a plurality of tongue members 134 adapted for attachment to a portion of the cranium, such as the occipital bone. The tongue members 134 can have a butterfly-like arrangement and be securely connected at a common junction 136. The tongue members 134 can be movable in both lateral and vertical dimensions to facilitate attachment to the cranium (e.g., the occipital bone).

Each of the tongue members 134 can include a plurality of openings 138. For example, each of the tongue members 134 can include three circular openings 138. It will be appreciated, however, that the tongue members 134 can include one, four, or even more openings 138. The openings 138 may be adapted for mating with a screw or pin (not shown) to facilitate attachment of the first clamp member $40_a$ to the cranium (e.g., the occipital bone). The first clamp member $40_a$ can be made of any one or combination of medical grade materials, such as stainless steel, titanium, or other known metal alloy.

Figure 8A:
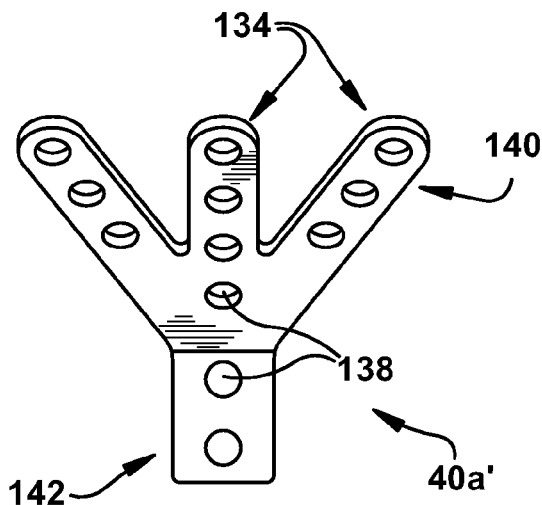
FIG. 8A is a top view showing an alternative embodiment of the clamp member in FIG. 3I.
Figure 8B:
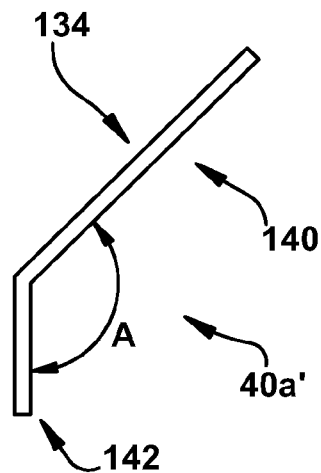
FIG. 8B is a side view of the clamp member in FIG. 8A.

An alternative configuration of the first clamp member $40_a$ is shown in FIGS. 8A-B. As shown in FIGS. 8A-B, the first clamp member $40_a'$ can have a Y-shaped configuration and include a first end portion 140 integrally formed with a second end portion 142. The first end portion 140 can include a plurality of spaced apart tongue members 134 for attachment to a portion of the cranium, such as the occipital bone. Each of the tongue members 134 can include a plurality of openings 138 adapted for mating with a screw or pin (not shown). The second end portion 142 can also include a plurality of openings 138 adapted for mounting the first clamp member $40_a'$ to the receptacle portion 44. As shown in FIG. 8B, the first and second end portions 140 and 142 can form an angle A. The angle A can have any desired value, such as about 45° depending on the anatomy of the bony structure and the size of the first clamp member $40_a'$. It will be appreciated that the clamp member $40_a'$ can alternatively have the configuration shown in FIG. 12. For example, two of the tongue members 134 can be fused to form a V-shaped configuration, while a third tongue member is in communication with the V-shaped tongue members.

Figure 9:
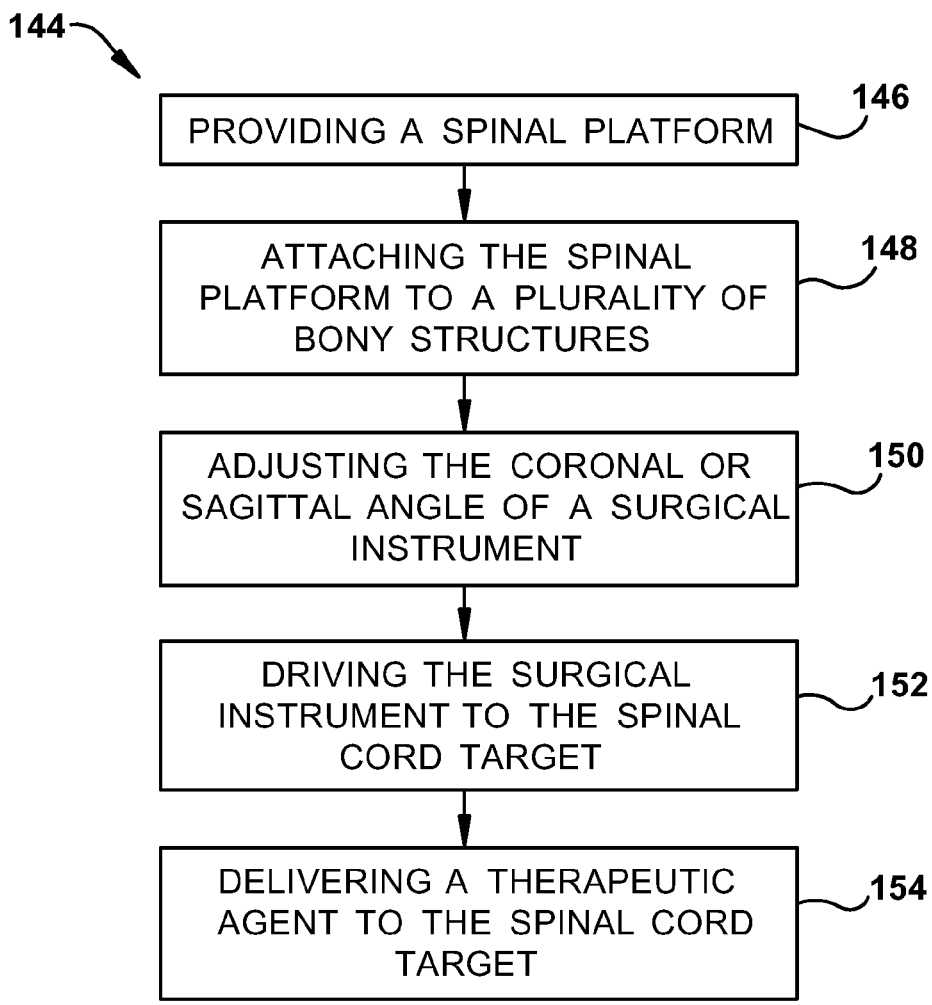
FIG. 9 is a process flow diagram illustrating a method for delivering a therapeutic agent to a spinal cord target according to another embodiment of the present invention.

FIG. 9 is a process flow diagram illustrating another aspect of the present invention. In FIG. 9, a method 144 is provided for delivering a therapeutic agent to a spinal cord target using the spinal platform 10 illustrated in FIGS. 1A-B. Although the method 144 is illustrated with reference to delivering a therapeutic agent to the ventral horn (not shown in detail), it will be appreciated that the therapeutic agent can be delivered to any portion of the spinal cord parenchyma and the structures associated therewith, such as the grey matter, white matter, central canal, spinal nerve, the dorsal root ganglia, and the dorsal or ventral roots.

The spinal cord target can be selected based on a number of anatomical and physiological factors, including the accessibility of the spinal cord target and the type of disease or disorder being treated. Where a subject is suffering from a motor neuron disease, for example, the spinal cord target can comprise the ventral horn as the ventral horn includes motor nuclei of the somatic nervous system. As used herein, the term "subject" can refer to any animal, including, but not limited to, humans and non-human animals (e.g., rodents, arthropods, insects, fish (e.g., zebrafish), non-human primates, ovines, bovines, ruminants, lagomorphs and porcines. A variety of other nervous system diseases or disorders can be treated according to the present method including, but not limited to, neuropathies, injuries of the spinal cord, demyelinating diseases, pain, spasticity, and infiltrating tumors of the spinal cord.

The type and amount of therapeutic agent delivered to the spinal cord target will depend on the type and severity of the nervous system disease being treated. As used herein, the term "therapeutic agent" can refer to any substance that, when administered in a therapeutically effective amount to a subject suffering from a nervous system disease, has a therapeutic beneficial effect on the health and well-being of the subject. A therapeutic beneficial effect on the health and well-being of a subject includes, but it not limited to: (1) curing the disease; (2) slowing the progress of the disease; (3) causing the disease to retrogress; or (4) alleviating one or more symptoms of the disease.

The term "therapeutic agent" can also include any substance that, when administered to a subject known or suspected of being particularly susceptible to a disease, has a prophylactic beneficial effect on the health and well-being of the subject. A prophylactic beneficial effect on the health and well-being of a subject includes, but is not limited to: (1) preventing or delaying on-set of the disease in the first place; (2) maintaining a disease at a retrogressed level once such level has been achieved by a therapeutically effective amount of a substance (which may be the same as or different from the substance used in a prophylactically effective amount); or (3) preventing or delaying recurrence of the disease after a course of treatment with a therapeutic ally effective amount of a substance (which may be the same as or different from the substance used in a prophylactically effective amount).

Non-limiting examples of therapeutic agents that can be delivered to the spinal cord target can include small molecules (i.e., organic compounds, whether naturally-occurring or artificially created that have relatively low molecular weight and that do not include proteins, polypeptides, or nucleic acids), polypeptides, polynucleotides, viral vectors, and cell transplants, such as immune cell transplants (e.g., macrophage and T cells) and fetal or adult progenitor cells, i.e., any totipotent stem cell, pluripotent stem cell, and multipotent stem cell, as well as any of their lineage descendant cells that have the capacity to differentiate into a specific type of cell. Therapeutic agents can be delivered to the spinal cord target to affect nervous tissue function immediately or, alternatively, delivered as part of a controlled or sustained release for calculated release into the nervous tissue comprising the spinal cord target.

Where a subject is afflicted with a motor neuron disease, for example, a therapeutically effective amount of fetal progenitor cells can be delivered to the ventral horn of the subject according to the method 144. As used herein, the term "therapeutically effective amount" can refer to that amount of a therapeutic agent that relieves to some extent one or more symptoms of a nervous system disease or disorder, or returns to normal, either partially or completely, one or more physiological or biochemical parameters associated with or causative of the nervous system disease or disorder.

As shown in FIG. 9, the method 144 can include providing a spinal platform 10 at Step 146. Prior to providing the spinal platform 10, however, the spinal cord target can be assessed using any one or combination of known imaging modalities (e.g., CT, MRI, etc.) to evaluate the anatomy at (and surrounding) the spinal cord target. For example, the dimensions of the dorsal lamina and the spinous process, as well as the thickness of the lateral white column surrounding the ventral horn can be determined using CT and/or MRI either prior to or during the procedure to achieve real-time targeting. Once the anatomical dimensions of the spinal cord target have been determined, the spinal platform 10 can be selected for use.

The spinal cord target can be accessed by performing a laminectomy. The length or size of the laminectomy can be adjusted depending on the length of the spinal cord target that requires treatment. Where the spinal cord target is located between T3 and T5, for example, a surgical site can be determined by counting rostrally from T7 and caudally from T1. The subject can then be placed in a prone position, and the operative field prepared with alcohol and betadyne prior to draping. An incision (not shown) having a length sufficient to allow positioning of the spinal platform 10 about the spinal cord target can be made over the spine. Next, a multi-level laminectomy can be performed over the thoracic spinal cord. Following laminectomy, an incision (not shown) of about 2 cm can be made through the dura mater with the aid of a dural guide (not shown) to expose the spinal cord. The dura mater may then be reflected away from the pial layer using a suture, followed by a pial incision at the injection site using a scalpel (not shown).

After exposing the spinal cord target, the spinal platform 10 can be attached to the spinal column at Step 148. To attach the spinal platform 10, the brace member 12 can be positioned at or below the level of the paraspinal muscles (not shown) in the incision. It will be appreciated that the spinal platform 10 can alternatively be positioned above the paraspinal muscles using a minimally invasive surgical approach. Next, the first and second clamp members 40 and 42 can be attached to the spinous processes of T3 and T5 by positioning the arm portion 46 of the clamp body 34 and the contacting portion 62 of the clamp pin 36 about the lateral aspects of the spinous processes. A tightening tool (e.g., a hex wrench) (not shown) can then be used to tighten the arm portion 46 and the clamp pin 36 about the spinous processes.

Once the brace member 12 has been secured to the vertebral column, the carriage member 14 can be moved in either an anterior or posterior direction so that the channel 88 of the carriage member and the channel 118 of the universal joint 94 are positioned over the spinal cord target. After appropriately positioning the carriage member 14, the first and second locking mechanisms 100 and 102 may be operated by tactile force to engage the first longitudinal rail 20 and thereby securely position the carriage member over the spinal cord target.

Figure 10:
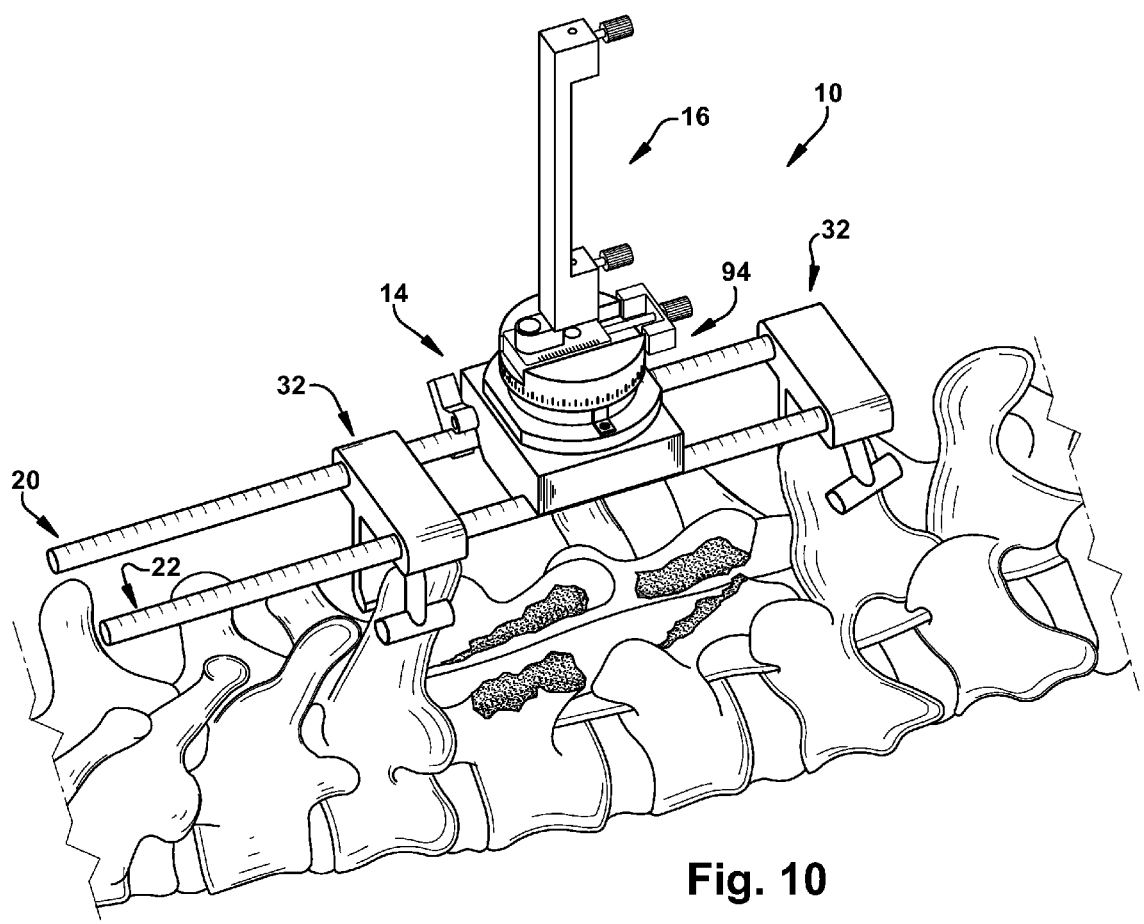
FIG. 10 is a perspective view showing the spinal platform in FIGS. 1A-B mounted to a vertebral column.
Figure 11:
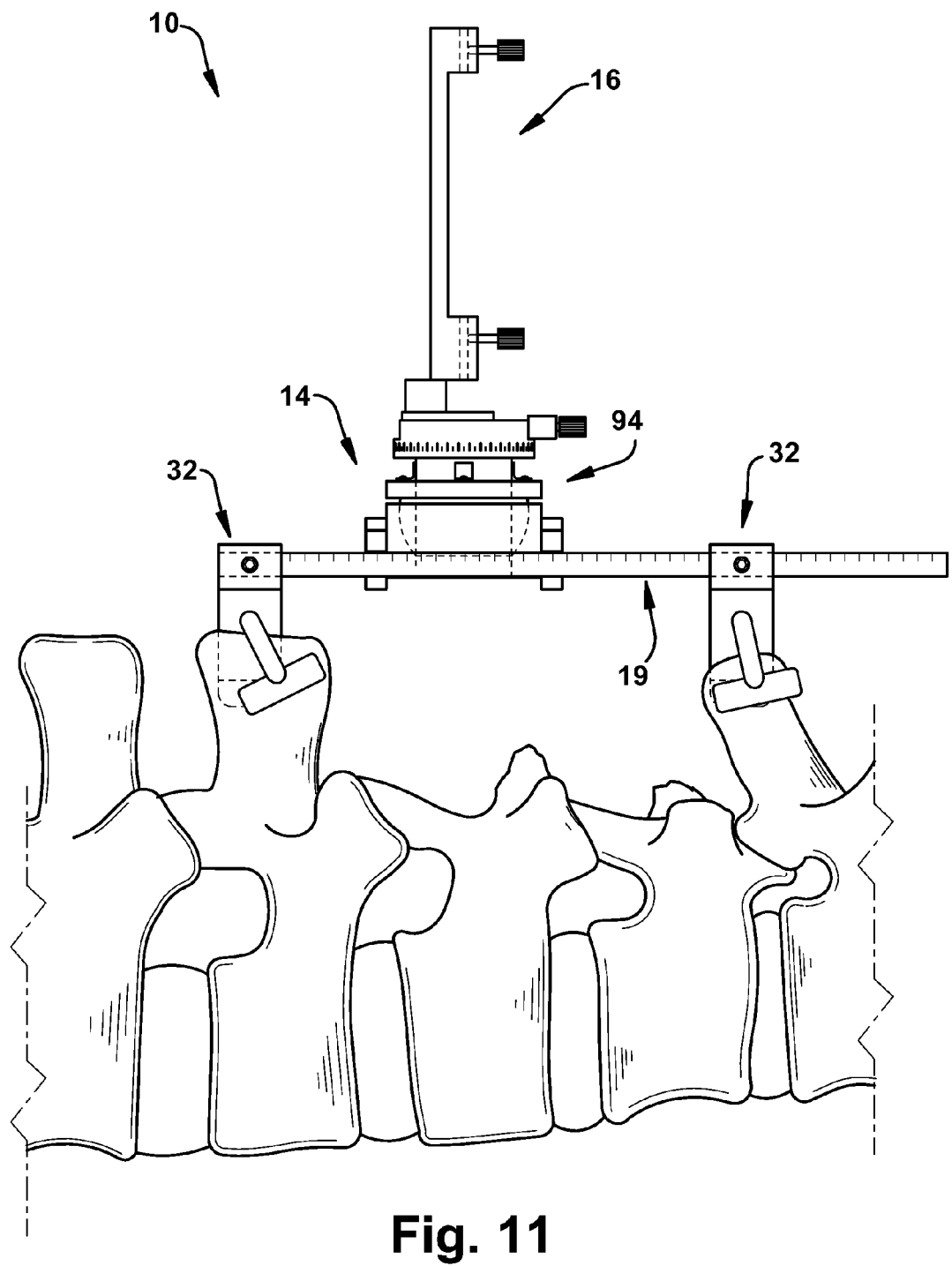
FIG. 11 is a perspective view showing a different view of the spinal platform in FIG. 10.

Next, the spinal platform 10 can be fully assembled by operably connecting the universal joint 94 to the micromanipulator 16 (FIGS. 10-11). Once the spinal platform 10 has been completely assembled, a surgical instrument 126 (e.g., a cannula) can be operably mounted to the micromanipulator 16 (FIG. 1A). At Step 150 (FIG. 9), the coronal or sagittal angle of the surgical instrument 126 can be adjusted by manipulating the universal joint 94. For example, the universal joint 94 can be positioned so that the coronal or sagittal angle of the surgical instrument 126 is substantially orthogonal to the plane of the surface of the spinal cord, thereby allowing for accurate targeting of the ventral horn or previously identified spinal cord target. Alternatively, intraoperative real-time imaging, such as ultrasound, MRI, optical coherence tomography, or CT can be used to guide targeting. In such a case, the coronal and/or sagittal angles can be adjusted to match the desired trajectory to the spinal cord target. If it has not been done so already, the surgical instrument 126 can be operably connected to the pump 18 via a fluid delivery line 132.

At Step 152, the surgical instrument 126 can then be driven along a constrained trajectory to the spinal cord target via the micromanipulator 16. It will be appreciated that a real-time imaging technique, such as OCT imaging can be used to assist in accurately delivering the surgical instrument 126 to the spinal cord target. Additionally, it will be appreciated that the surgical instrument 126 can include an electrode (not shown) to assist in placing the surgical instrument via micro-electric recording. To deliver the therapeutic agent to the ventral horn, a distal tip (not shown in detail) of the surgical instrument 126 can be advanced through the marginal zone, the substantia gelatinosa, the body of the dorsal horn, and the intermediate horn of the spinal cord into a portion of the ventral horn, or other target, such as a demyelinated plaque (e.g., in multiple sclerosis) or the epicenter of trauma (e.g., in spinal cord injury).

Once the surgical instrument 126 is securely positioned at the spinal cord target, a therapeutically effective amount of the therapeutic agent can be delivered to the spinal cord target at Step 154. For example, a therapeutically effective amount of fetal progenitor cells can be infused into the fluid delivery line 132 via the pump 18 at an appropriate rate and concentration. The fetal progenitor cells may then be delivered to the ventral horn to mitigate or prevent symptoms associated with the motor neuron disease. By consolidating the micromanipulator 16 and the pump 18 along with the brace member 12, the present invention allows precise and controlled delivery of therapeutic agents to the spinal cord.

Following successful delivery of the therapeutic agent to the spinal cord target, the surgical instrument 126 (along with the entire spinal platform 10) may be removed from the subject and the incision then closed in four layers. For example, the dura mater can be closed with a running stitch (not shown), in a watertight fashion, using a 4-0 Nurolon suture. A strip of Gelfoam (not shown) can be placed over the closure. A 0 Vicryl suture (not shown) can then be used for the deep muscular layer, obliterating the dead space and reducing the potential for developing epidural hematoma. The second layer, the fascia, may also be closed with a 0 Vicryl suture (not shown) in a watertight fashion. The dermal layer can then be closed with 2-0 Vicryl sutures (not shown) followed by skin stapling.

Figure 12:
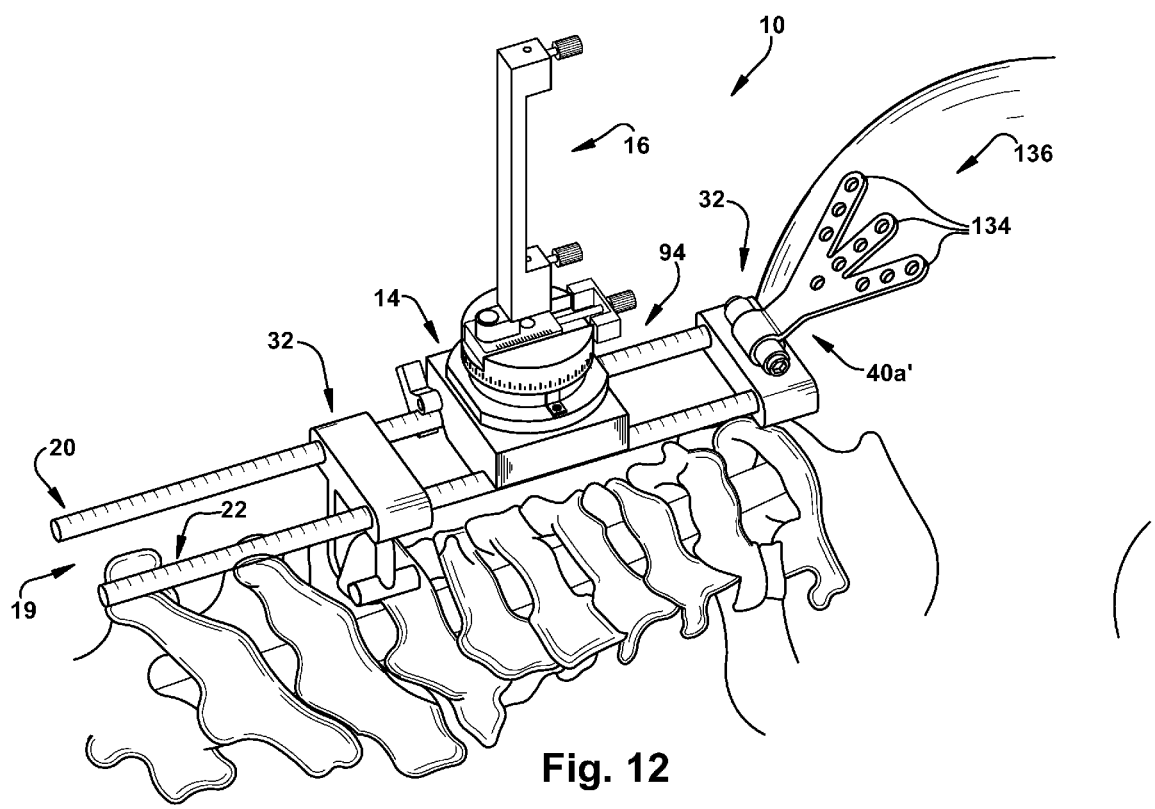
FIG. 12 is a perspective view showing the spinal platform in FIGS. 7A-B mounted to a vertebral column and the occipital bone.

It will be appreciated that the spinal platform $10_a$ illustrated in FIGS. 7A-B can also be used to deliver a therapeutic agent to a spinal cord target via a method similar to the one described above. Where the spinal cord target is located between C3 and C4, for example, an incision can be made to expose the vertebrae. After performing a laminectomy, the brace member 12 can be attached to the bony structure by first attaching the second clamp member 42 to a spinous process (as described above), followed by attachment of the first clamp member $40_a'$ to the occipital bone (FIG. 12). As shown in FIG. 12, the tongue members 134 of the first clamp member $40_a'$ can be positioned adjacent the occipital bone. Next, a plurality of screws or pins (not shown) can be used to secure each of the tongue members 134 to the occipital bone.

After the brace member 12 is securely attached to the bony structures, the rest of the spinal platform $10_a$ can be assembled as described above. Once the spinal platform $10_a$ is assembled, a surgical instrument 126 (e.g., a cannula) can be used to deliver a therapeutic agent to the spinal cord target (as described above). Advantageously, the first clamp member $40_a'$ allows the spinal platform $10_a$ to be positioned above the cervical spine for delivery of a therapeutic agent to the cervical portion of the spinal cord.

Another aspect of the present invention is illustrated in FIGS. 13-19G. The spinal platform $10_b$ shown in FIGS. 13-19G can be identically constructed as the spinal platform 10 shown in FIGS. 1A-6B, except as described below. In FIGS. 13-19G, structures that are identical as structures in FIGS. 1A-6B use the same reference numbers, whereas structures that are similar but not identical carry the suffix "b".

Figure 13:
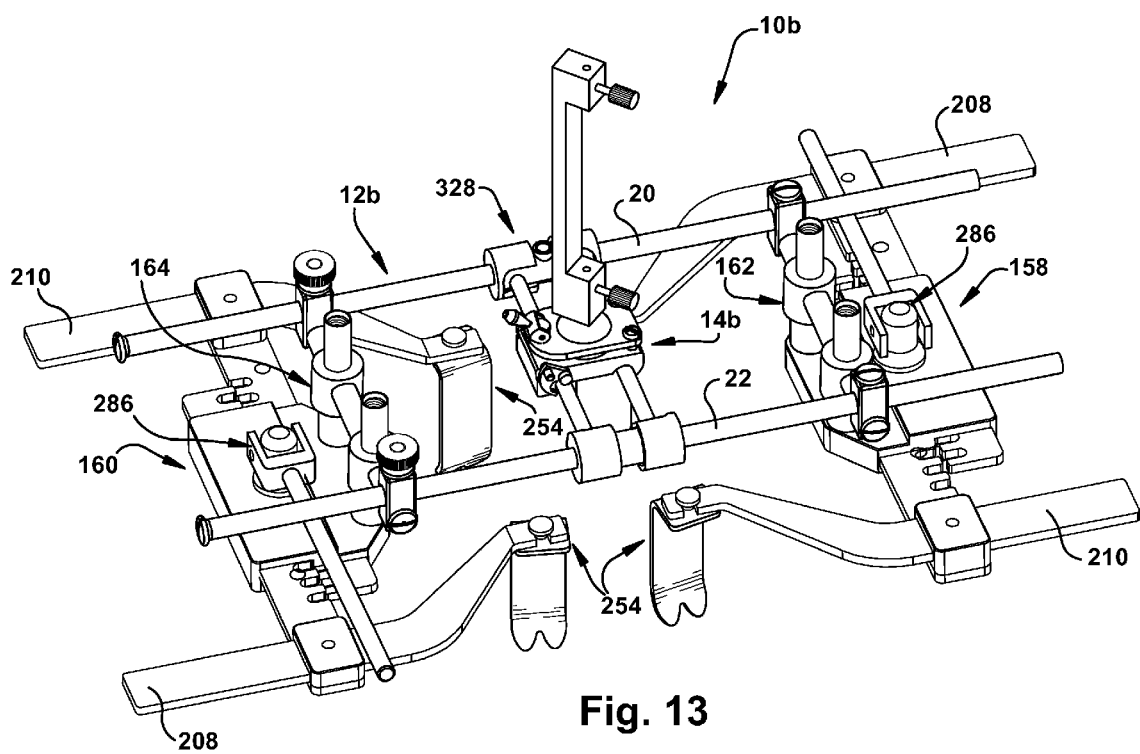
FIG. 13 is a perspective view of a spinal platform constructed in accordance with another aspect of the present invention.

As shown in FIG. 13, the spinal platform $10_b$ can comprise a brace member $12_b$, a carriage member $14_b$ operatively coupled to and movable along the brace member, a universal joint $94_b$ for adjusting the coronal or sagittal angle of a surgical instrument (not shown), and first and second tissue retracting members 158 and 160. As described in more detail below, the spinal platform $10_b$ provides an optimized system that maximizes the length of incisions required for injection of a therapeutic agent into the spinal cord, while simultaneously providing a stabilized platform for precise and controlled delivery of the therapeutic agent. Access to the spinal cord may be achieved with the minimal incision necessary for exposure to the spinal cord, through minimally-invasive tubular retractors (not shown), or through an entirely percutaneous procedure guided by real-time imaging.

Figure 14A:
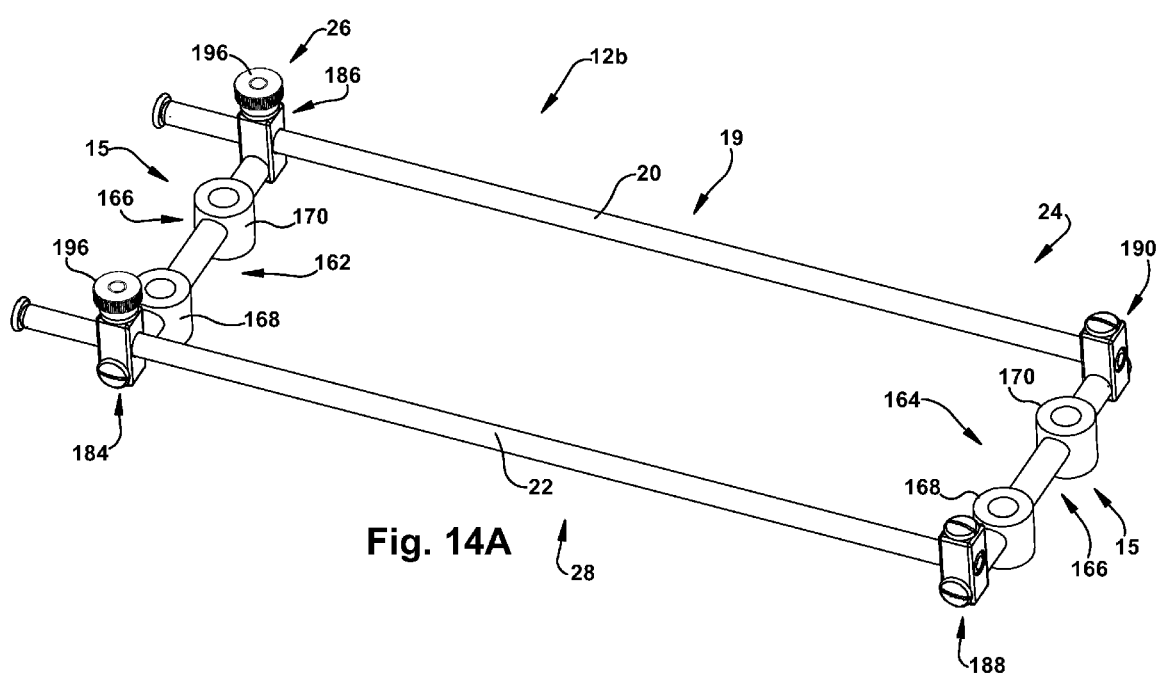
FIG. 14A is a perspective view showing a brace member of the spinal platform in FIG. 13.
Figure 14B:
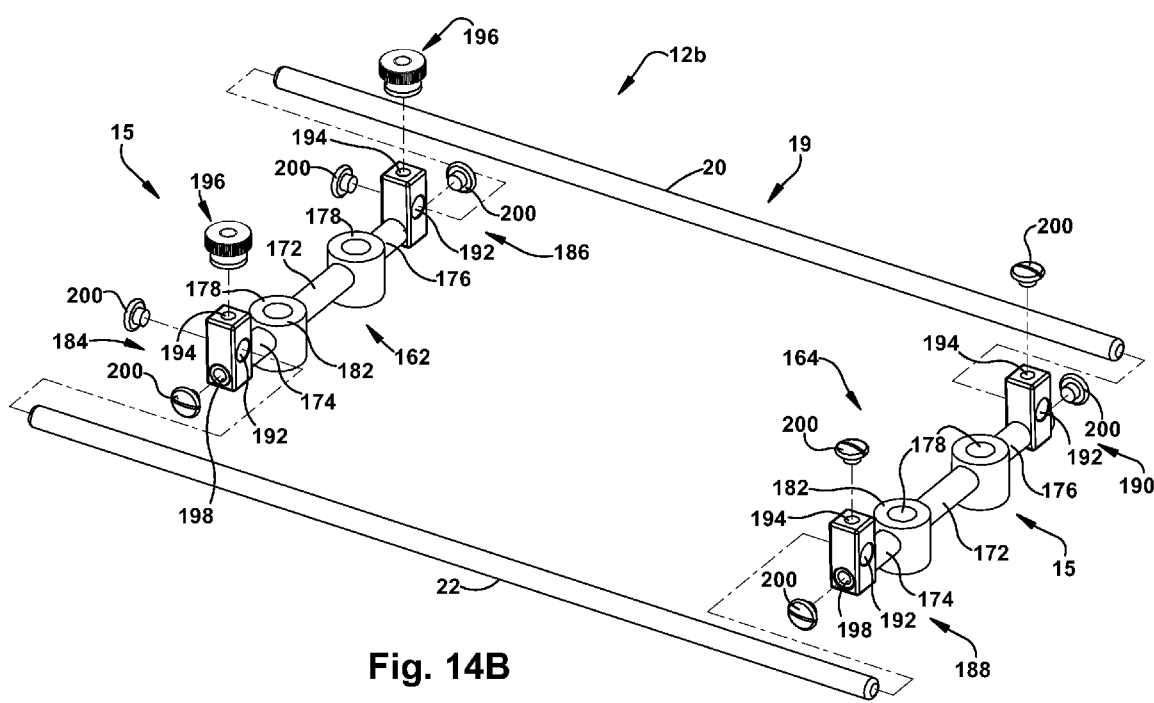
FIG. 14B is an exploded perspective view showing the brace member in FIG. 14A.

Referring to FIGS. 14A-B, the brace member $12_b$ of the spinal platform $10_b$ can comprise a plurality of attachment members 15 for securing the brace member to a plurality of bony structures surrounding at least a portion of a spinal cord target. The plurality of attachment members 15 can be operably connected to and extend between oppositely disposed first and second longitudinal rails 20 and 22. Each of the first and second longitudinal rails can include a distal end portion 24, a proximal end portion 26, and a middle portion 28 extending between the proximal and distal end portions. It will be appreciated that the brace member $12_b$ can include any number of longitudinal rails 19.

Each of the plurality of attachment members 15 can include first and second base members 162 and 164. As shown in FIGS. 14A-B, the first base member 162 can be operably secured to the proximal end portion 26 of each of the first and second longitudinal rails 20 and 22, and the second base member 164 can be operably secured to the distal end portion 24 of each of the first and second longitudinal rails. Each of the first and second base members 162 and 164 can comprise a cross bar 166 having first and second cylindrical screw mounts 168 and 170. Each of the screw mounts 168 and 170 (FIG. 14B) can be integrally formed with and situated between a rod-shaped center section 172, a first rod-shaped outer section 174, and a second rod-shaped outer section 176. Each of the screw mounts 168 and 170 can include a channel 178 for receiving a percutaneous post 180 (FIGS. 16A-B), an upper surface 182 (FIGS. 14A-B), and a lower surface (not shown in detail). It should be appreciated that the first and second outer sections 174 and 176 can have other shapes or configurations besides those illustrated in FIGS. 14A-B. The first and second base members 162 and 164 can be made of any one or combination of medical grade materials, such as stainless steel, titanium, or other known metal alloy.

The brace member $12_b$ can also include first, second, third, and fourth pivot members 184, 186, 188, and 190 for securing the first and second longitudinal rails 20 and 22 to the first and second base members 162 and 164. Each of the first and second pivot members 184 and 186 can have a rectangular configuration and respectively include a longitudinal channel 192 (FIG. 14B) for receiving the second and first longitudinal rails 22 and 20, respectively. Additionally, each of the first and second pivot members 184 and 186 can include a first securing channel 194 that extends perpendicular to, and is in fluid communication with, the longitudinal channel 192. The first securing channel 194 can be adapted to receive a knurled nut 196 for securing the first and second longitudinal rails 20 and 22. As shown in FIG. 14B, each of the first and second pivot members 184 and 186 can also include a second securing channel 198 for receiving the first and second outer sections 174 and 176 of the first base member 162, respectively. Screws 200 (e.g., pan head screws) can be placed into the second securing channel 198 of each of the first and second pivot members 184 and 186, and then mated with the first and second outer sections 174 and 176 to secure the first base member 162 between the first and second longitudinal rails 20 and 22.

As shown in FIG. 14B, each of the third and fourth pivot members 188 and 190 can have a rectangular configuration and respectively include a longitudinal channel 192 for receiving the second and first longitudinal rails 22 and 20, respectively. Additionally, each of the third and fourth pivot members 188 and 190 can include a first securing channel 194 that extends perpendicular to, and is in fluid communication with, the longitudinal channel 192. The first securing channel 194 may be adapted to receive a screw 200 (e.g., a pan head screw) for securing the first and second longitudinal rails 20 and 22. Additionally, each of the third and fourth pivot members 188 and 190 can include a second securing channel 198 for receiving the first and second outer sections 174 and 176 of the second base member 164, respectively. Screws 200 (e.g., pan head screws) can be placed into the second securing channel 198 of each of the third and fourth pivot members 188 and 190, and then mated with the first and second outer sections 174 and 176 to secure the second base member 164 between the first and second longitudinal rails 20 and 22.

It will be appreciated that the pivot members 184, 186, 188, and 190 are rotatable about the first and second outer sections 174 and 176 of the first and second base members 164 and 166. The rotatable design of the pivot members 184, 186, 188, and 190 allows multiple degrees of freedom of the spinal platform $10_b$ when positioned over the spinal cord target. For example, the rotatable design permits the angle formed at the junction of the first pivot member 184 with the first outer section 174 to be greater or less than 90°. This is significant as the spine curves at different points and thus flexion of the spinal platform $10_b$ is necessary to ensure that the spinal platform does not shift or move excessively and risk unwanted movement of the surgical instrument.

Figure 15C:
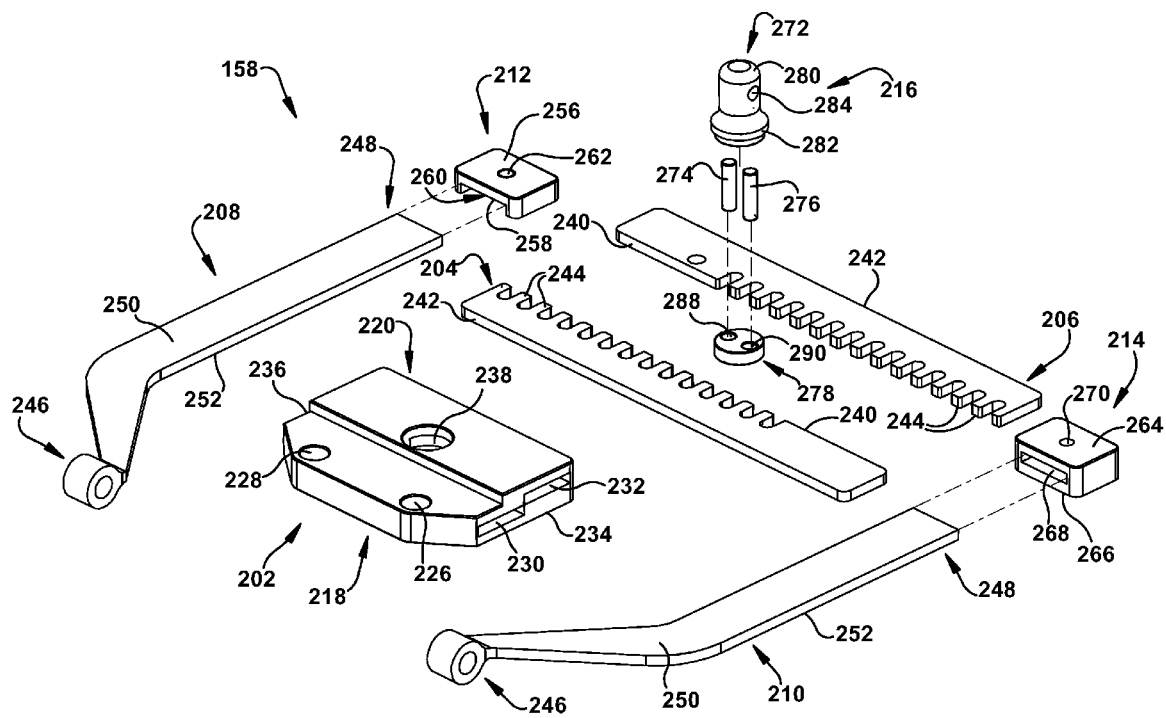
FIG. 15C is an exploded perspective view of the tissue retracting member in FIGS. 15A-B.

FIGS. 15A-C illustrate the first tissue retracting member 158; however, it should be appreciated that construction of the second tissue retracting member 160 can be identical to the construction of the first tissue retracting member, as described below. The first tissue retracting member 158 can comprise a mounting plate 202, first and second retractor racks 204 and 206, first and second retractor arms 208 and 210, first and second retractor arm retainers 212 and 214, and a retracting mechanism 216 for actuating the first and second retractor arms. The first tissue retracting member 158 can be made of any one or combination of medical grade materials, such as stainless steel, titanium, or other known metal alloy. Advantageously, the first and second tissue retracting members 158 and 168 can be married with the first and second base members 162 and 164, respectively, to provide a low profile spinal platform $10_b$ that maximizes the surgical field while minimizing the necessary incision.

As shown in FIG. 15C, the mounting plate 202 can comprise a distal end portion 218, a proximal end portion 220, a first major surface 222, and a second major surface 224 (FIG. 15B) oppositely disposed from the first major surface. The distal end portion 218 (FIG. 15C) of the mounting plate 202 can include first and second channels 226 and 228 extending between the first and second major surfaces 222 and 224. As described in more detail below, the first and second channels 226 and 228 may be adapted to receive a plurality of percutaneous posts 180 (FIGS. 16A-B). The mounting plate 202 (FIG. 15C) can also include third and fourth channels 230 and 232 extending between oppositely disposed first and second minor surfaces 234 and 236. The third and fourth channels 230 and 232 can be offset from one another, and can be adapted to receive the first and second retractor racks 204 and 206, respectively. As also shown in FIG. 15C, the mounting plate 202 can include a fifth channel 238 that extends between the first and second major surfaces 222 and 224, and is adapted to receive a portion of the retracting mechanism 216.

Each of the first and second retractor racks 204 and 206 can have an elongated, comb-like configuration and include oppositely extending first and second longitudinal edges 240 and 242. A substantial portion of the first longitudinal edge 240 of each of the first and second retractor racks 204 and 206 can include a plurality of teeth 244. For example, about two-thirds of the first longitudinal edge 240 of each of the first and second retractor racks 204 and 206 can include a plurality of teeth 244. As described in more detail below, the plurality of teeth 244 comprising a portion of the first longitudinal edge 240 of the first retractor rack 204 can be mated with the plurality teeth comprising the first longitudinal edge 240 of the of the second retractor rack 206 to form a part of the retracting mechanism 216.

Figure 15D:
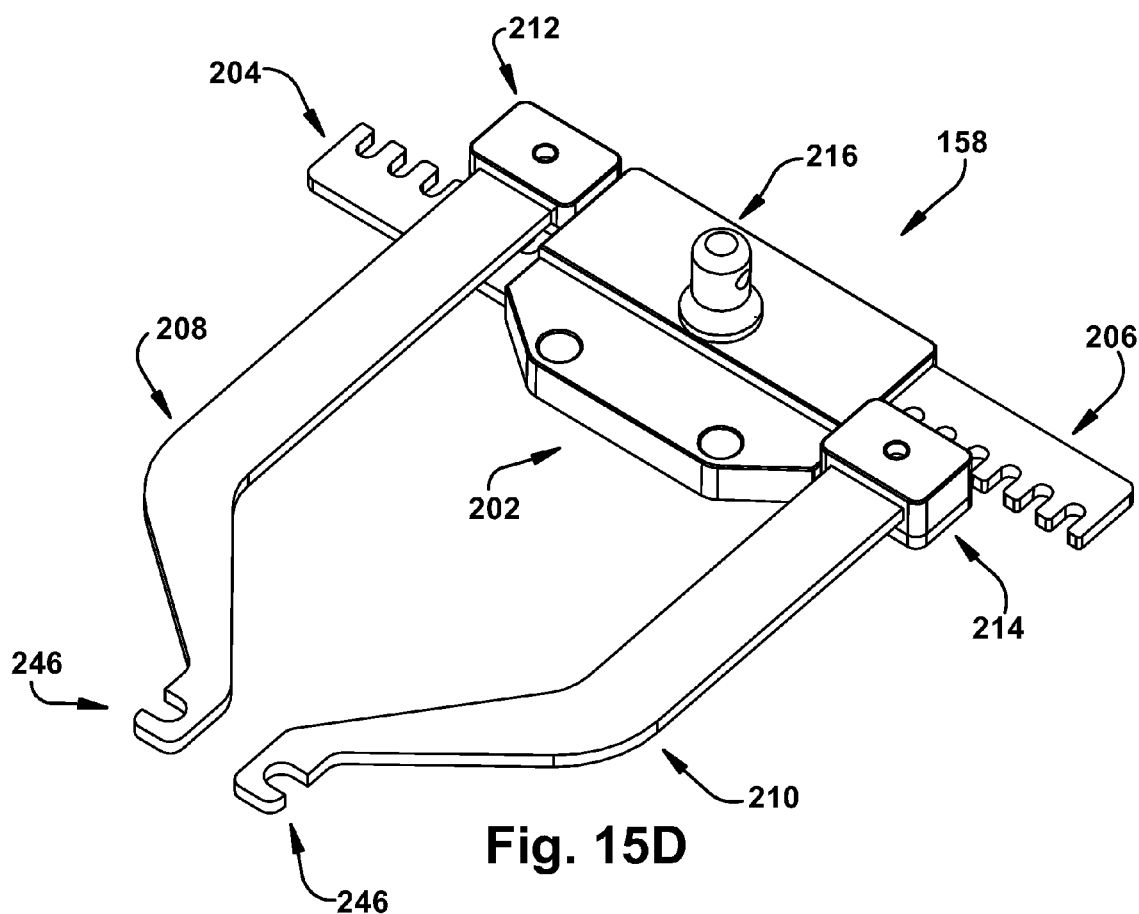
FIG. 15D is a perspective view showing the tissue retracting member in FIGS. 15A-B having an alternative distal end portion configuration.
Figure 15E:
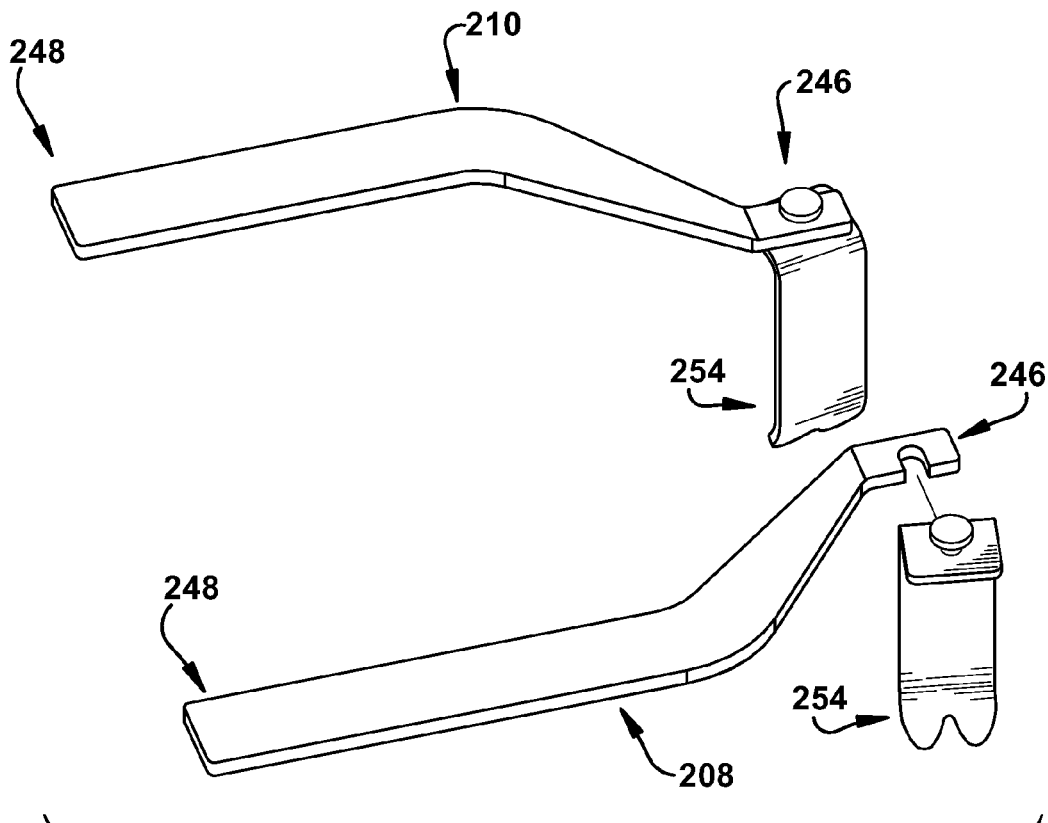
FIG. 15E is a perspective view showing the first and second retracting arms in FIG. 15D mated with respective tissue retractor blades.
Figures 15F, 15G:
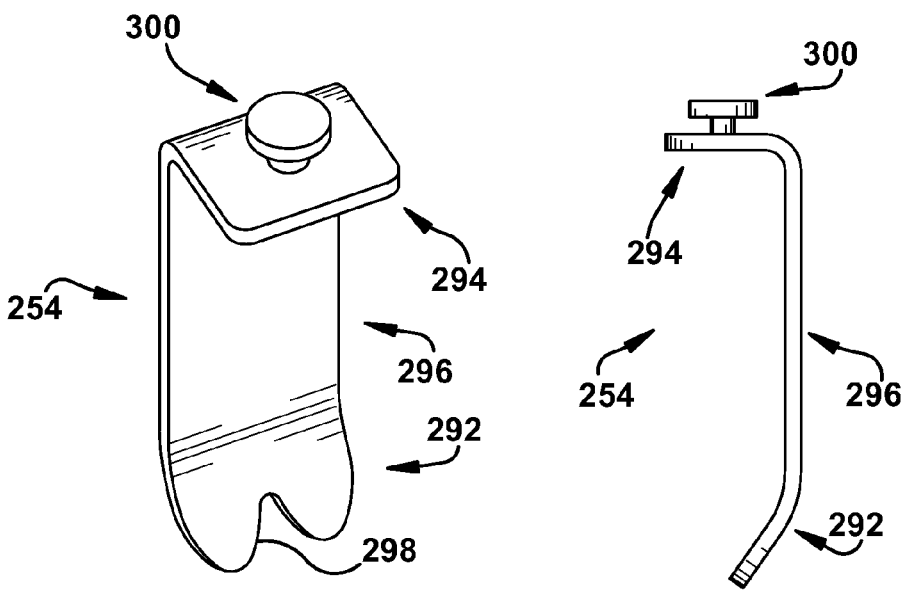
FIG. 15F is a perspective view of the tissue retractor blade shown in FIG. 15E.
FIG. 15G is a side view of the tissue retractor blade in FIG. 15F.

As shown in FIGS. 15A-C, the first and second retractor arms 208 and 210 can each include a distal end portion 246, a proximal end portion 248, and oppositely disposed first and second major surfaces 250 and 252. Each of the first and second retractor arms 208 and 210 can have a bent, L-shaped configuration and include a distal end portion 246 which is offset relative to the proximal end portion 248. The distal end portion 246 of each of the first and second retractor arms 208 and 210 can be adapted to receive a removable tissue retractor blade 254 (FIGS. 15E-G). For example, the distal end portion 246 (FIGS. 15A-C) of each of the first and second retractor arms 208 and 210 can have a tubular configuration. It should be appreciated that the distal end portion 246 of each of the first and second retractor arms 208 and 210 can have other configurations as well. For instance, the distal end portion 246 of each of the first and second retractor arms 208 and 210 can have a flattened, C-shaped configuration (FIGS. 15D-E).

The first tissue retracting member 158 can also include first and second retractor arm retainers 212 and 214 for receiving the proximal end portion 248 of each of the first and second retractor arms 208 and 210, respectively. As shown in FIG. 15C, the first retractor arm retainer 212 can have a square-shaped configuration and include oppositely disposed first and second major surfaces 256 and 258. The second major surface 258 can define a groove 260 for receiving the proximal end portion 248 of the first retractor arm 208. The first retractor arm retainer 212 can also include a first channel 262 extending between the first and second major surfaces 256 and 258. The first channel 262 can be adapted to receive a screw or pin (not shown) to secure the proximal end portion 248 of the first retractor arm 208 in the groove 260.

The second retractor arm retainer 214 can have a square-shaped configuration and include oppositely disposed first and second major surfaces 264 and 266. As shown in FIG.

15C, the second retractor arm retainer 214 can include a receiving channel 268 for receiving the proximal end portion 248 of the second retractor arm 210. The second retractor arm retainer 214 can also include a second channel 270 extending between the first major surface 264 and the receiving channel 268. The second channel 270 can be adapted to receive a screw or pin (not shown) to secure the proximal end portion 248 of the second retractor arm 210 in the receiving channel 268.

Referring to FIG. 15C, the retracting mechanism 216 can comprise a capstone body 272, a first pin 274, a second pin 276, and a capstone washer 278. The capstone body 272 can have a pear-shaped configuration and include a cylindrical first end portion 280 integrally formed with an outwardly-flared second end portion 282. The first end portion 280 can include an axially-extending actuating channel 284 adapted to mate with an actuating tool 286 (FIG. 13). The second end portion 282 of the capstone body 272 can include first and second ports (not shown) adapted to receive the first and second pins 274 and 276. The capstone washer 278 can have a rounded configuration and include first and second channels 288 and 290 for receiving the first and second pins 274 and 276, respectively.

As shown in FIGS. 15E-G, each of the tissue retracting blades 254 can have an elongated, C-shaped configuration and include a tissue contacting portion 292, a mating portion 294, and a main body portion 296 extending between the tissue contacting portion and the mating portion. The tissue contacting portion 292 can have a curved or arcuate shape relative to the main body portion 296, and include a V- or U-shaped indentation 298 to facilitate tissue displacement. The mating portion 294 can also have a curved or arcuate shape relative to the main body portion 296. Additionally, the mating portion 294 can include a T-shaped stem member 300 for mating with the distal end portion 246 of each of the first and second retractor arms 208 and 210. The tissue retracting blades 254 can be made of any one or combination of medical grade materials, such as stainless steel, titanium, or other known metal alloy, or MRI-compatible material, such as carbon fiber.

In operation, the first tissue retracting member 158 can be assembled by inserting the first and second retractor racks 204 and 206 into the third and fourth channels 230 and 232 of the mounting plate 202, respectively. After the first and second retractor racks 204 and 206 have been inserted into the third and fourth channels 230 and 232, the plurality of teeth 244 of the first retractor rack 204 can be mated with the plurality of teeth of the second retractor rack 206. Next, the first and second retractor arms 208 and 210 can be mated with the first and second retractor arm retainers 212 and 214, respectively. The first and second retractor arm retainers 212 and 214 can then be mated with the first and second retractor racks 204 and 206 (respectively). The retracting mechanism 216 can then be assembled by inserting the capstone washer 278 into the third channel 230 of the mounting plate 202, and then placing the first and second pins 274 and 276 into the first and second channels 288 and 290 of the capstone washer 278. Next, the capstone body 272 can be mated with the first and second pins 274 and 276 to completely assemble the retracting mechanism 216. Application of the first and second tissue retracting members 158 and 160 is described in greater detail below.

The spinal platform $10_b$ can also include a plurality of percutaneous posts 180 (FIGS. 16A-B). As shown in FIGS. 16A-B, each of the percutaneous posts 180 can have an elongated, cylindrical configuration and a length L. The length L of the percutaneous post 180 can be defined by a distal end portion 302, a proximal end portion 304, and a middle portion 306 extending between the distal and proximal end portions. Each of the percutaneous posts 180 can also include a threaded inner bore 308 extending between the distal and proximal end portions 302 and 304. The percutaneous posts 180 can be made of any one or combination of medical grade materials, such as stainless steel, titanium, or other known metal alloy, or MRI-compatible material, such as carbon fiber. As described in more detail below, the percutaneous posts 180 can be inserted through the first and second channels 226 and 228 of the mounting plate 202, as well as the screw mounts 168 and 170 of the first and second base members 162 and 164 to secure the spinal platform $10_b$ to the plurality of bony structures.

The threaded inner bore 308 of the percutaneous posts 180 can be adapted to receive a plurality of self-tapping screw 310 (FIG. 16D). As shown in FIG. 16C, each of the plurality of self-tapping screws 310 can have a length L' defined by a proximal end portion 312, a distal end portion 314, and a middle portion 316 extending between the proximal and distal end portions. The proximal end portion 312 can include a polygonal-shaped mating portion 318 adapted to mate with a tightening tool (e.g., a hex wrench) (not shown). The self-tapping screw 310 can also include a tapered threaded portion 320 integrally formed with the mating portion 318. The tapered threaded portion 320 can be adapted to mate with the inner threaded bore 308 at the proximal end portion 304 of the percutaneous post 180 (FIG. 16D). The middle portion 316 of the self-tapping screw 310 can comprise an elongated shaft 322 that terminates at the distal end portion 314. The distal end portion 314 can have pointed end 324 and include a plurality of threads 326 for boring into a bony structure (e.g., vertebral lamina). The length L' of the self-tapping screw 310 can be greater than the length L of the percutaneous post 180 so that the distal end portion 314 of the self-tapping screw can extend beyond the distal end portion 302 of the percutaneous post (FIG. 16D). The greater length L' of the self-tapping screw 310 promotes anchoring of the percutaneous post 180 to a bony structure.

Figure 17:
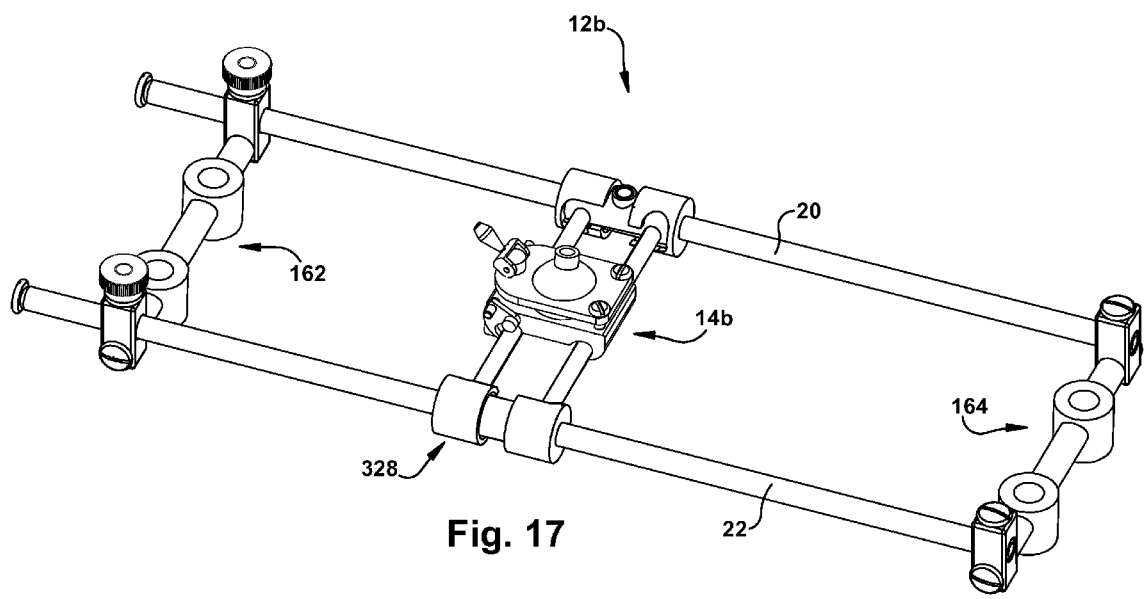
FIG. 17 is a perspective view showing a brace member, a carriage member, a universal joint, and a gondola of the spinal platform in FIG. 13.
Figure 18A:
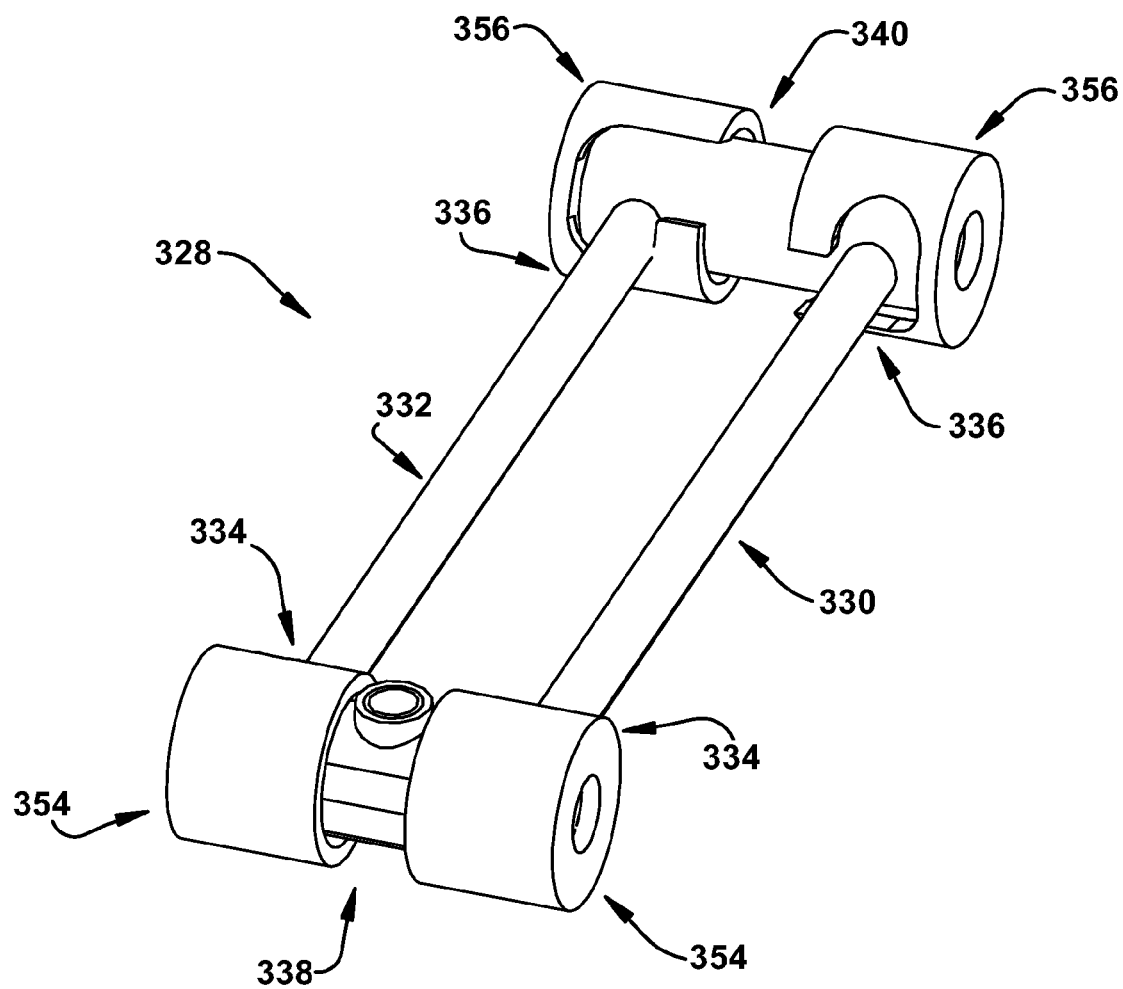
FIG. 18A is a perspective view of the gondola in FIG. 17.
Figure 18B:
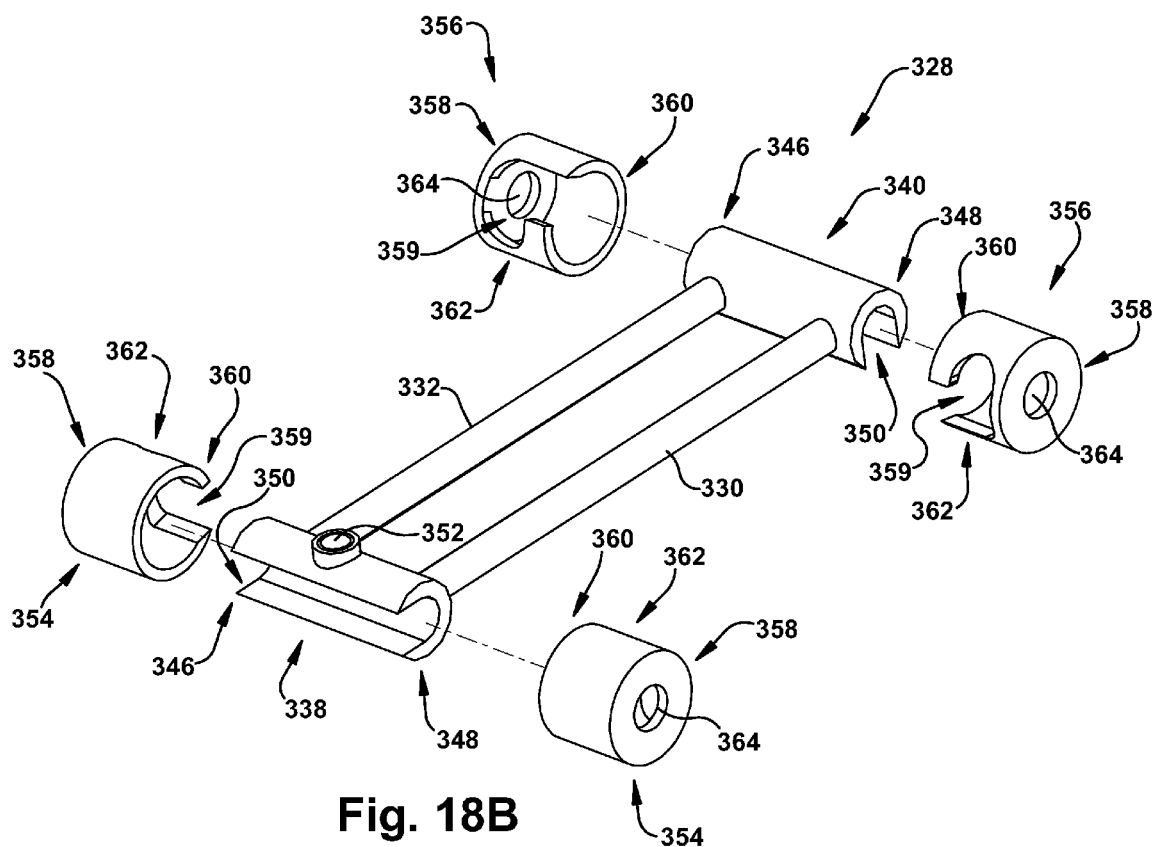
FIG. 18B is an exploded perspective view of the gondola in FIG. 18A.

As shown in FIG. 17, the carriage member $14_b$ can be operatively coupled to the brace member $12_b$ via a gondola 328. The gondola 328 can be slidably mounted to and axially situated between the first and second longitudinal rails 20 and 22. The gondola 328 (FIG. 18A) can comprise first and second parallel tracks 330 and 332. Each of the first and second tracks 330 and 332 can include first and second ends 334 and 336 that are integrally formed with first and second cylindrical mating portions 338 and 340, respectively. The first and second mating portions 338 and 340 can each have a C-shaped cross-sectional configuration and include a first end 346, a second end 348, and a groove 350 extending between the first and second ends (FIG. 18B). The groove 350 of the first and mating portion 338 and the groove of the second mating portion 340 can be adapted to receive the first and second longitudinal rails 20 and 22, respectively. As shown in FIG. 18B, the first mating portion 338 of the gondola 328 can include an axial channel 352 in fluid communication with the groove 350. The axial channel 352 can be adapted to receive a screw or pin (not shown) for securing the first longitudinal rail 20 to the first mating portion 338.

The gondola 328 can also include a plurality of first and second keeper members 354 and 356 for securing the first and second mating portions 346 and 348, respectively, to the first and second longitudinal rails 20 and 22. Each of the first and second keeper members 354 and 356 can have a generally tubular configuration and include a first end 358, a second end 360, and a cylindrical main body 362 extending between the first and second ends. The main body 362 of each of the first and second keeper members 354 and 356 can include an L-shaped cut-out section 359 for mating with the first and second tracks 330 and 332, respectively. The first end 358 of the first keeper member 354 can include a port 364 for receiving the first longitudinal rail 20, and the first end of the second keeper member 356 can include a port 364 for receiving the second longitudinal rail 22. As shown in FIG. 18A, the second end 360 of the first and second keeper members 354 and 356 can be mated with the first and second mating portions 338 and 340. Mating the second end 360 of the first and second keeper members 354 and 356 with the first and second mating portions 338 and 340 ensures that the gondola 328 is operably secured to the brace member $12_b$ (FIG. 17).

Figure 19A:
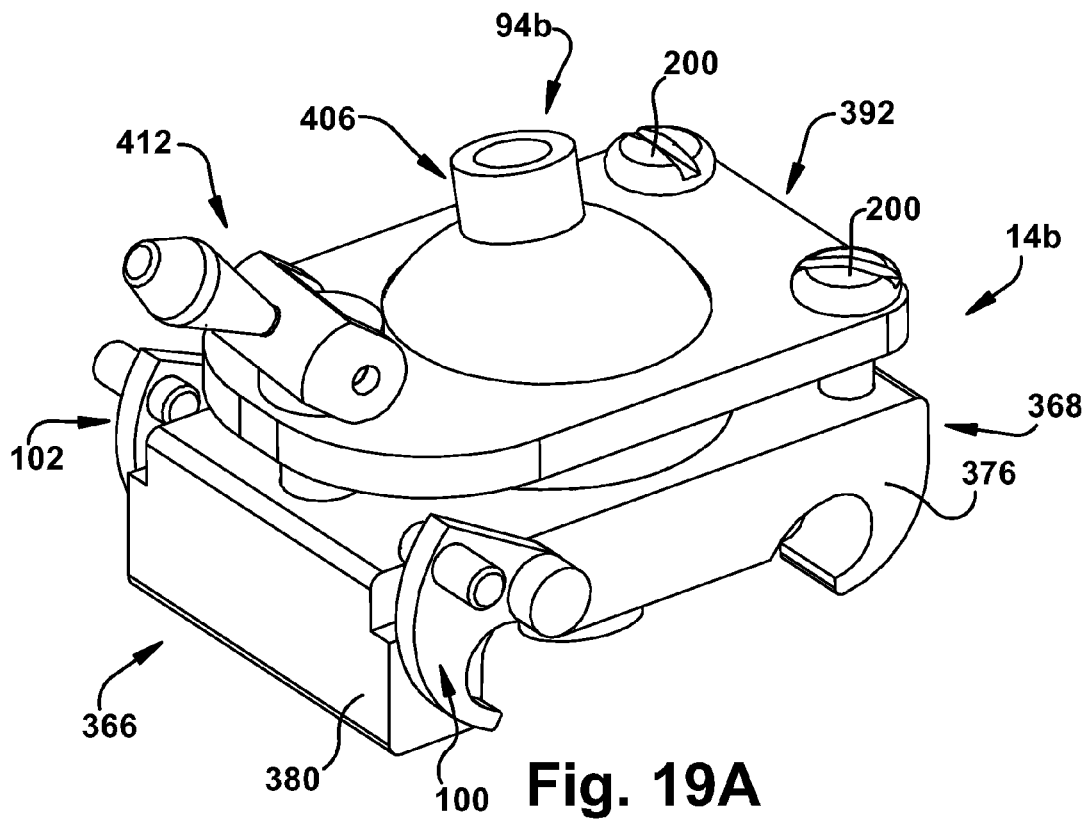
FIG. 19A is a perspective view showing the top of the carriage member and universal joint in FIG. 17.
Figure 19B:
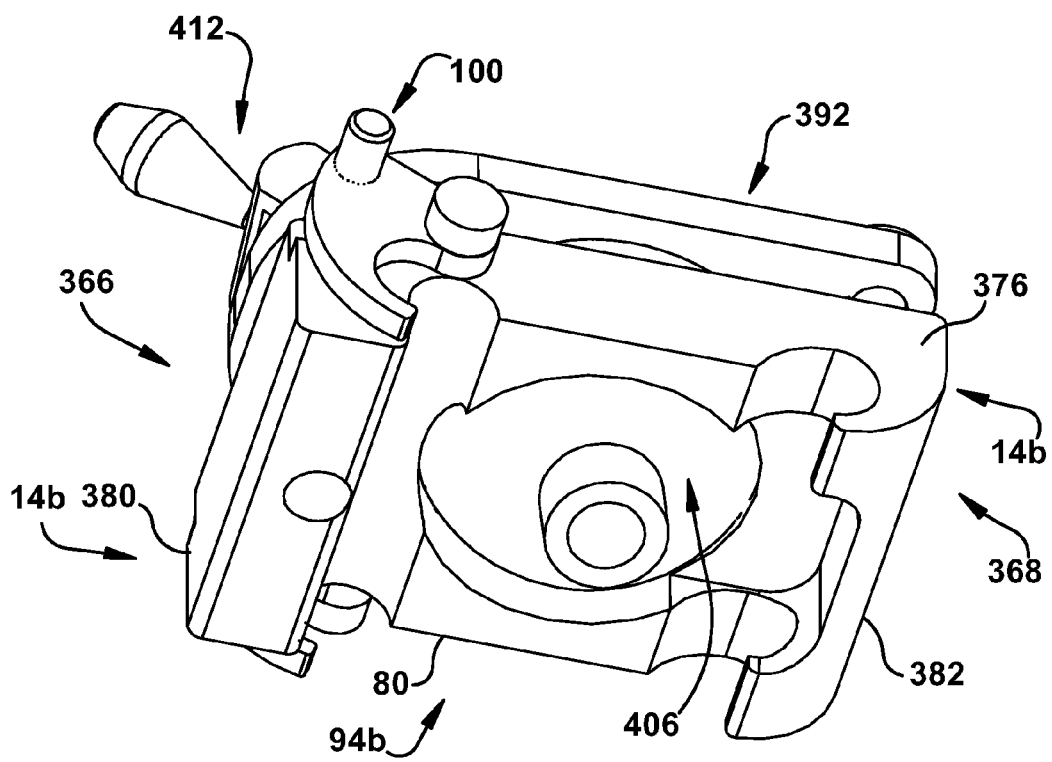
FIG. 19B is a perspective view showing the bottom of the carriage member and the universal joint in FIG. 19A.
Figure 19C:
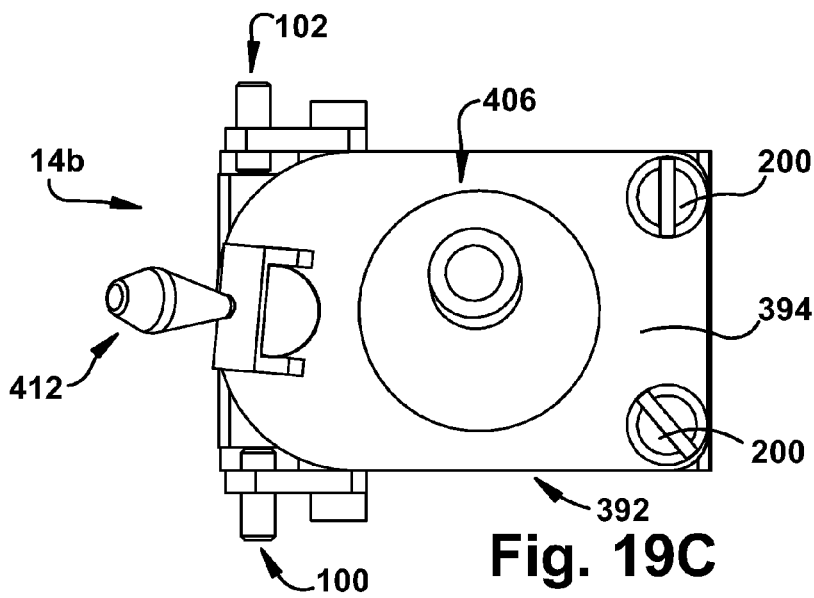
FIG. 19C is an alternative perspective view of the carriage member and the universal joint in FIG. 19A.
Figure 19D:
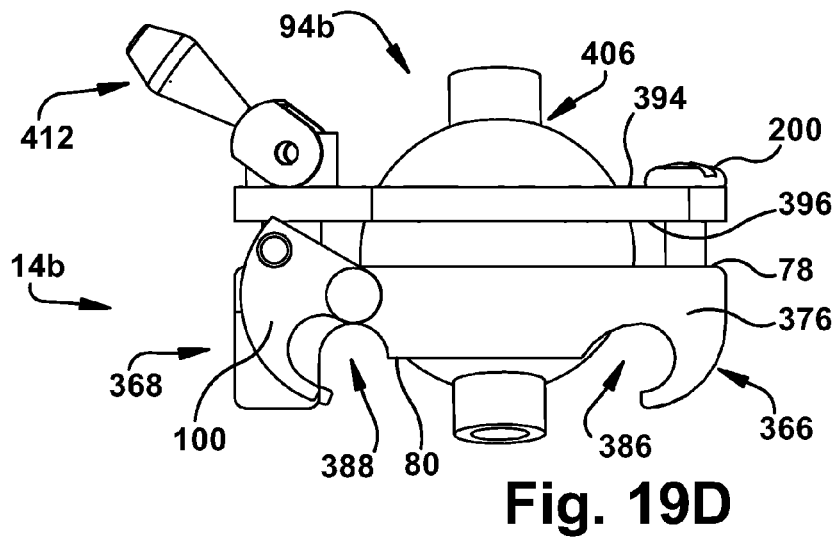
FIG. 19D is a side view of the carriage member and universal joint in FIG. 19C.
Figure 19E:
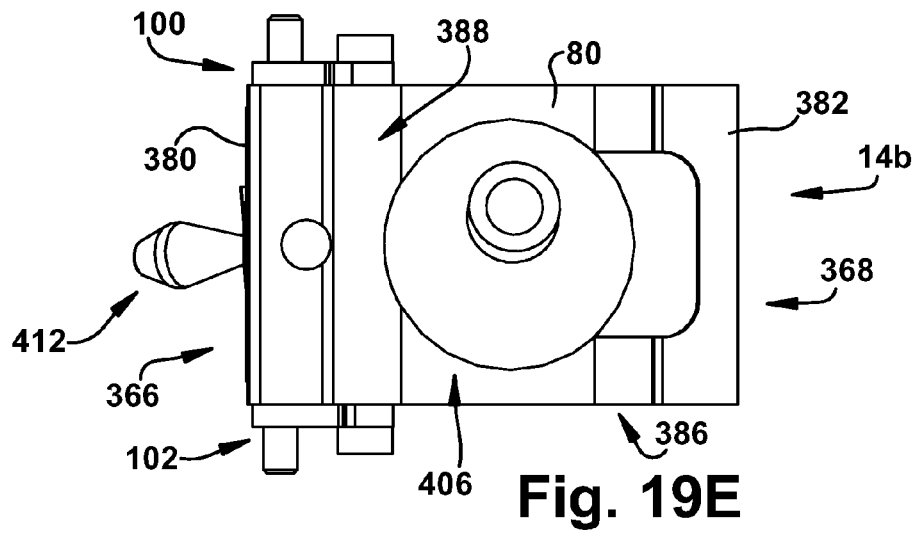
FIG. 19E is a top plan view of the carriage member and universal joint in FIG. 19D.
Figure 19F:
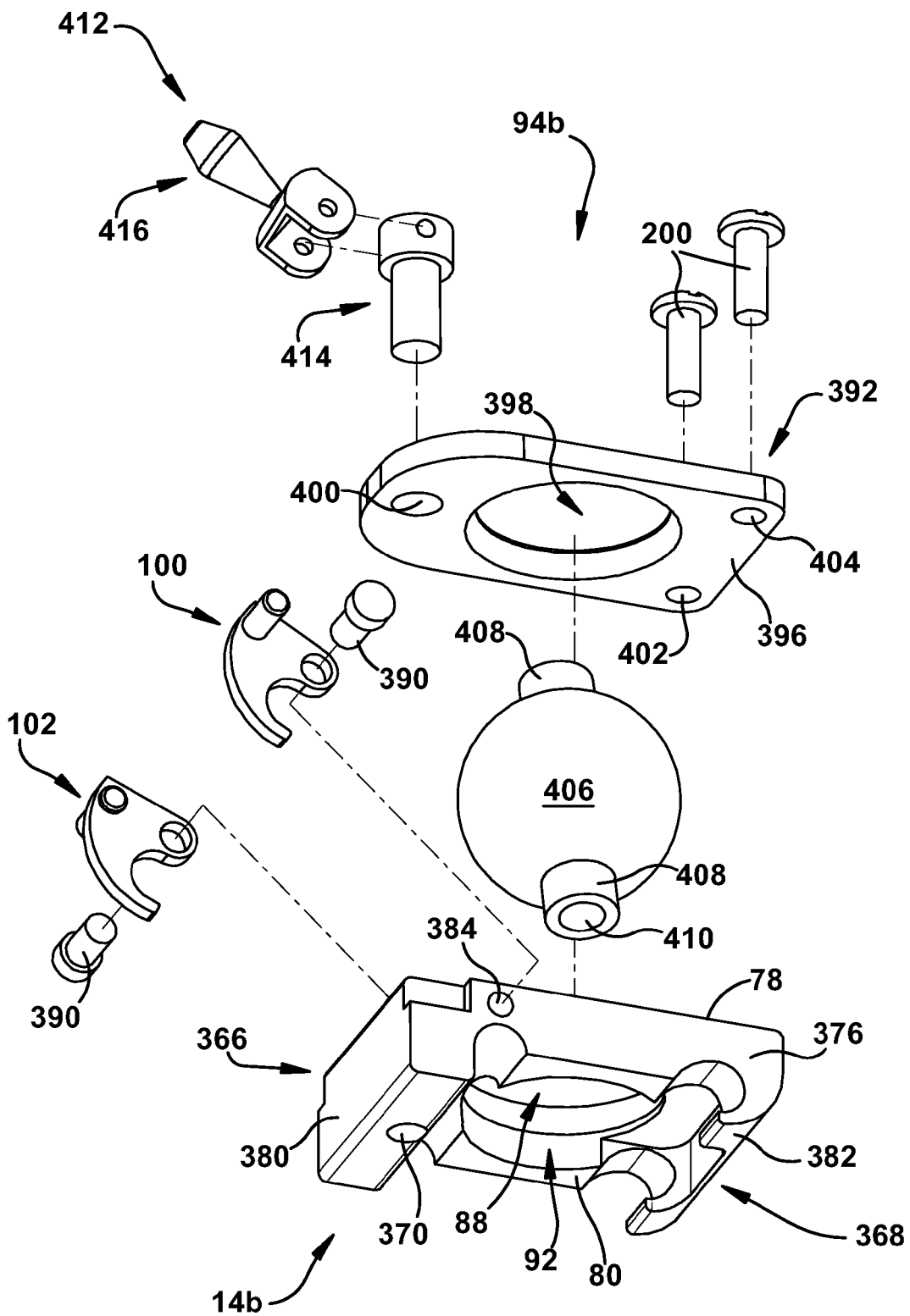
FIG. 19F is an exploded perspective view of the carriage member and the universal joint in FIG. 19E.
Figure 19G:
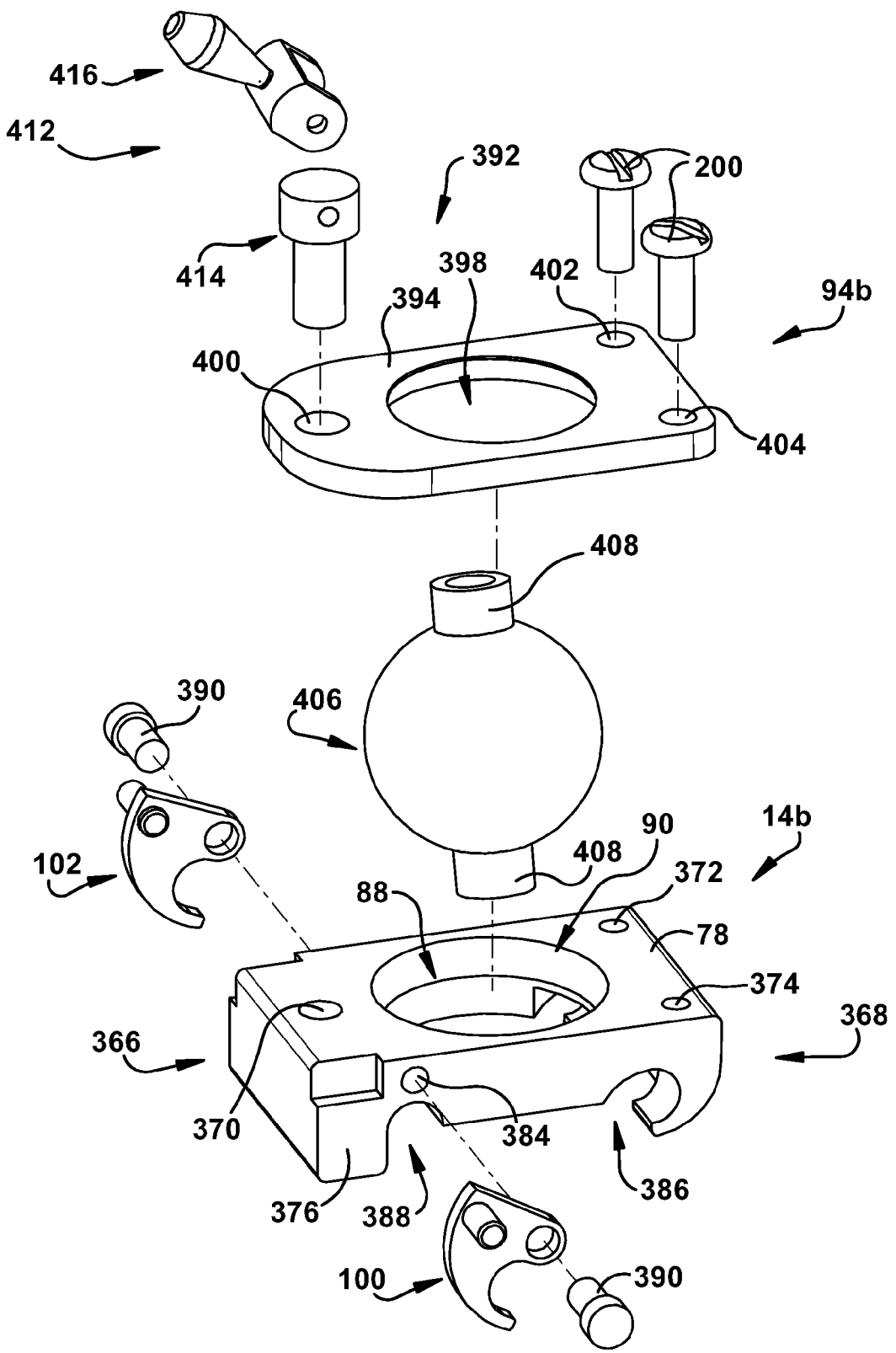
FIG. 19G is an alternative exploded perspective view of the carriage member and the universal joint in FIG. 19F.

The carriage member $14_b$ (FIGS. 19A-G) can comprise a main body 366 having oppositely disposed first and second major surfaces 78 and 80, a bowl-shaped channel 88 extending between the first and second major surfaces, and a plurality of oppositely disposed locking mechanisms 100 and 102, each of which can be separately attached to the main body. As shown in FIGS. 19F-G, the main body 366 of the carriage member $14_b$ can comprise a lower block 368 having first, second, and third channels 370, 372, and 374 extending between the first and second major surfaces 78 and 80. The lower block 368 can include a first major side surface 376 oppositely disposed from a second major side surface 378 (FIG. 19D). Additionally, the lower block 368 (FIG. 19G) can include a first minor side surface 380 oppositely disposed from a second minor side surface 382 (FIG. 19E). The first and second major side surfaces 376 and 378 (FIG. 19G), as well as the first minor side surface 380 can have a flattened configuration. The second minor side surface 382 (FIG. 19E) can have an arcuate shape. As described in more detail below, the lower block 368 (FIG. 19F) can include a plurality of locking channels 384 adapted to mate with the locking mechanisms 100 and 102.

As shown in FIG. 19G, the second major surface 80 of the lower block 368 can include first and second tracks 386 and 388 for receiving the first and second tracks 330 and 332 of the gondola 328, respectively. The first and second tracks 386 and 388 can have a semi-circular cross-sectional shape and extend between the first and second major side surfaces 376 and 378 of the lower block 368. A portion of each of the first and second tracks 386 and 388 can also be in fluid communication with the channel 88 that extends between the first and second major surfaces 78 and 80 of the lower block 368. As shown in FIGS. 19F-G, the channel 88 can have a bowl-shaped configuration and can include a first opening 90 located at the first major surface 78 of the lower block 368, and a second opening 92 located at the second major surface 80 of the lower block. The diameter of the first opening 90 can be greater than the diameter of the second opening 92. As described in more detail below, the bowl-shaped configuration of the channel 88 facilitates free rotation of the universal joint $94_b$ when seated in the channel.

The carriage member $14_b$ can also include first and second locking mechanisms 100 and 102 for securing the carriage member at a desired location along the gondola 328. As shown in FIGS. 19F-G, the first and second locking mechanisms 100 and 102 can be operably attached to the first and second major side surfaces 376 and 378 of the lower block 368, respectively. The first and second locking mechanisms 100 and 102 can be operably attached to the lower block 368 via a plurality of pins 390 that extend through each of the locking mechanisms into the plurality of locking channels 384. Each of the first and second locking mechanisms 100 and 102 can have a Y-shaped configuration and include a mating portion 104 and a tensioning portion 106. The mating portion 104 has a C-shaped configuration and can be adapted for contacting a portion of the second track 332 of the gondola 328. The tensioning portion 106 can be integrally formed with the mating portion 104 and have a stem-like configuration to facilitate movement of the mating portion (i.e., by tactile force).

As shown in FIGS. 19F-G, the carriage member $14_b$ can additionally include a clamp plate 392 for securing the universal joint $94_b$ in the bowl-shaped channel 88 of the lower block 368. The clamp plate 392 can have a bullet-shaped configuration and include oppositely disposed first and second major surfaces 394 and 396. The second major surface 396 can be adapted for mating with the first major surface 78 of the lower block 368. The clamp plate 392 can include a major channel 398 extending between the first and second major surfaces 394 and 396. As described below, the major channel 398 can be adapted to receive a portion of the universal joint $94_b$. Additionally, the clamp plate 392 (FIG. 19G) can include first, second, and third channels 400, 402, and 404 for mating with the first, second, and third channels 370, 372, and 374 of the lower block 368.

Referring to FIGS. 19A-E, the universal joint $94_b$ can be seated in the bowl-shaped channel 88 of the lower block 368. The universal joint $94_b$ (FIGS. 19F-G) can comprise a spherical member 406 having oppositely disposed tubular members 408 that are integrally formed with the spherical member. The spherical member 406 can also include a channel 410 that extends between the tubular members 408. The channel 410 can be adapted to receive a surgical instrument, such as cannula for delivery of a therapeutic agent to a spinal cord target.

In operation, the carriage member $14_b$ and the universal joint $94_b$ can be married by placing the spherical member 406 in the bowl-shaped channel 88 of the lower block 368 and then mating the second major surface 396 of the clamp plate 392 with the first major surface 78 of the lower block. If it has not been done so already, the first and second locking mechanisms 100 and 102 can be securely mated with the lower block 368. Next, a plurality of screws 200 (e.g., pan head screws) can be separately inserted through the second and third channels 402 and 404 of the clamp plate 392 and the second and third channels 372 and 374 of the lower block 368 so that the clamp plate is securely mated with the lower block. After securing the clamp plate 392 to the lower block 368, a universal joint locking mechanism 412 can be inserted into the third channel 404 of the clamp plate 392 and the third channel 374 of the lower block 368. As shown in FIGS. 19F-G, the universal joint locking mechanism 412 can comprise a lock post 414 and a cam lock 416. As described in greater detail below, the universal joint locking mechanism 412 can be actuated to secure the universal joint $94_b$ in the bowl-shaped channel 88 of the lower block 368.

Figure 20:
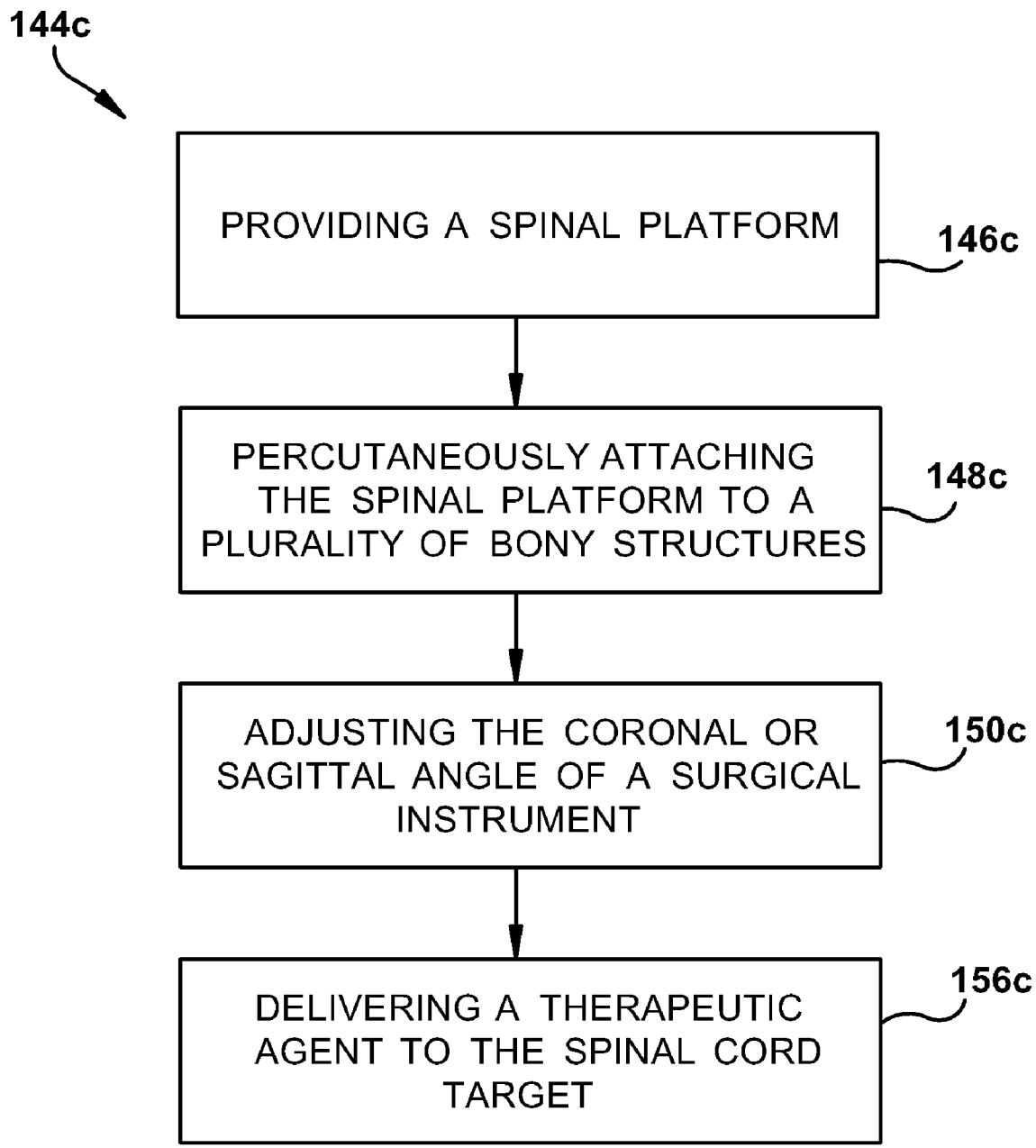
FIG. 20 is a process flow diagram illustrating a method for delivering a therapeutic agent to a spinal cord target according to another aspect of the present invention.

Another aspect of the present invention is illustrated in FIGS. 20-23. In FIGS. 20-23, a method $144_c$ is provided for delivering a therapeutic agent to a spinal cord target. The steps of the method $144_c$ illustrated in FIGS. 20-23 can be identical to the steps of the method 144 described in FIGS. 9-12, except as described below. In FIG. 20, steps that are identical as steps in FIG. 9 use the same reference numbers, whereas steps that are similar but not identical carry the suffix "c". Although the method $144_c$ is illustrated with reference to delivering a therapeutic agent to a thoracic portion of the spinal cord, it will be appreciated that that the method can also be employed to deliver a therapeutic agent to any other portion of the spinal cord. Additionally, it will be appreciated that the method $144_c$ can be employed to deliver a therapeutic agent to any portion of the spinal cord parenchyma and the structures associated therewith, such as the grey matter, white matter, central canal, spinal nerve, the dorsal root ganglia, and the dorsal or ventral roots.

The spinal cord target can be selected based on a number of anatomical and physiological factors, including the accessibility of the spinal cord target and the type of disease or disorder being treated. Where a subject is suffering from a motor neuron disease, for example, the spinal cord target can comprise the ventral horn (not shown) as the ventral horn includes motor nuclei of the somatic nervous system. A variety of other nervous system diseases or disorders, such as those provided above can be treated according to the method. As discussed above, the type and amount of therapeutic agent delivered to the spinal cord target will depend on the type and severity of the nervous system disease being treated, as well as the nature of the therapeutic agent.

Non-limiting examples of therapeutic agents that can be delivered to the spinal cord target can include small molecules (i.e., organic compounds, whether naturally-occurring or artificially created that have relatively low molecular weight and that do not include proteins, polypeptides, or nucleic acids), polypeptides, polynucleotides, viral vectors, and cell transplants, such as immune cell transplants (e.g., macrophage and T cells) and fetal or adult progenitor cells, i.e., any totipotent stem cell, pluripotent stem cell, and multipotent stem cell, as well as any of their lineage descendant cells that have the capacity to differentiate into a specific type of cell. Therapeutic agents can be delivered to the spinal cord target to affect nervous tissue function immediately or, alternatively, delivered as part of a controlled or sustained release for calculated release into the nervous tissue comprising the spinal cord target. Where a subject is afflicted with a motor neuron disease, for example, a therapeutically effective amount of fetal progenitor cells can be delivered to the ventral horn of the subject according to the method $144_c$.

As shown in FIG. 20, Step $146_c$ of the method $144_c$ can include providing a spinal platform $10_b$. Prior to providing the spinal platform $10_b$, however, the spinal cord target can be assessed using any one or combination of known imaging modalities (e.g., CT, MRI, etc.) to evaluate the anatomy at (and surrounding) the spinal cord target. For example, the dimensions of the dorsal lamina and the spinous process, as well as the thickness of the lateral white column surrounding the ventral horn can be determined using CT and/or MRI. Once the anatomical dimensions of the spinal cord target have been determined, a spinal platform $10_b$, such as the one illustrated in FIG. 13 can be selected for use.

The spinal cord target can be accessed by performing a laminectomy. The length of the laminectomy will depend on what length of treatment is needed for the spinal cord target. As described below, the length of exposed spinal cord can thus be adjusted by varying the position of the first and second base members 162 and 164 along the first and second longitudinal rails 20 and 22. Where the spinal cord target is located between T3 and T5, for example, a surgical site can be determined by counting rostrally from T7 and caudally from T1. The subject can then be placed in a prone position, and the operative field prepared with alcohol and betadyne prior to draping. An incision (not shown) can then be performed over the spine having a length sufficient to allow positioning of the spinal platform $10_b$ about the spinal cord target. Next, a multilevel laminectomy can be performed over the thoracic spinal cord. Following laminectomy, an incision (not shown) of about 2 cm can be made through the dura mater with the aid of a dural guide (not shown) to expose the spinal cord. The dura mater can then be reflected away from the pial layer using a suture, followed by a pial incision at the injection site using a scalpel (not shown). Alternatively, the pia may be left intact if the surgical instrument used for injection is sharp and capable of penetrating the spinal cord without compressing it.

Figure 21:
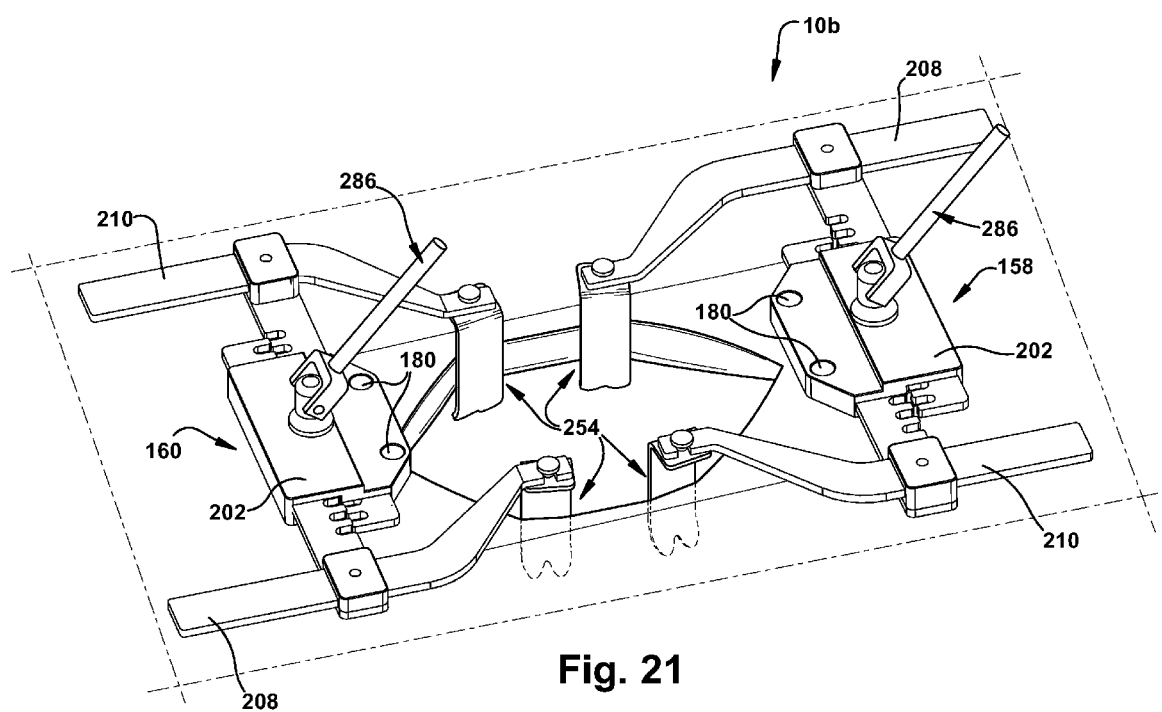
FIG. 21 is a perspective view showing first and second tissue retracting members secured to a spinal column.

After exposing the spinal cord target, the spinal platform $10_b$ can be assembled and then percutaneously attached to a plurality of bony structures at Step $148_c$. To attach the spinal platform $10_b$, the first and second tissue retracting members 158 and 160 can be oppositely positioned about the spinal cord target (FIG. 21). More particularly, the mounting plate 202 of each of the first and second tissue retracting members 158 and 160 can be positioned over T3 and T5 so that each tissue retractor blade 254 located at the distal end portion 246 of each of the first and second retractor arms 208 and 210 extend into the surgical field and contact the tissue surrounding the spinal cord target. Next, a plurality of percutaneous posts 180 can be inserted through the first and second channels 226 and 228 of the mounting plate 202 of each of the first and second tissue retracting members 158 and 160.

Next, a plurality of self-tapping screws 310 can be threaded (e.g., using a hex wrench; not shown) into the percutaneous posts 180 so that the pointed end 324 of each of the screws bores into the lamina above and below the laminectomy, a tightening tool 286 (FIG. 21) can be mated with the retracting mechanism 216 of each of the first and second tissue retracting members 158 and 160. The tightening tool 286 can then be manipulated (e.g., rotated in a clockwise or counter-clockwise manner) to distance the first and second retractor arms 208 and 210 from one another and thereby spread the tissue surrounding the spinal cord target.

It will be appreciated that the spinal platform $10_b$ can alternatively be attached to the spinal column prior to making the incision. For example, the first and second tissue retracting members 158 and 160 can be oppositely positioned about the spinal cord target so that the mounting plate 202 of each of the first and second tissue retracting members is positioned over T3 and T5. Next, a plurality of percutaneous posts 180 can be inserted through the first and second channels 226 and 228 of the mounting plate 202 of each of the first and second tissue retracting members 158 and 160. A plurality of self-tapping screws 310 can be threaded (e.g., using a hex wrench) into the percutaneous posts 180 so that the pointed end 324 of each of the screws bores into the lamina above and below the laminectomy. As described above, the incision can then be made about the spinal cord target, and the tissue surrounding the spinal cord target spread using the first and second tissue retracting members 158 and 160.

Figure 22:
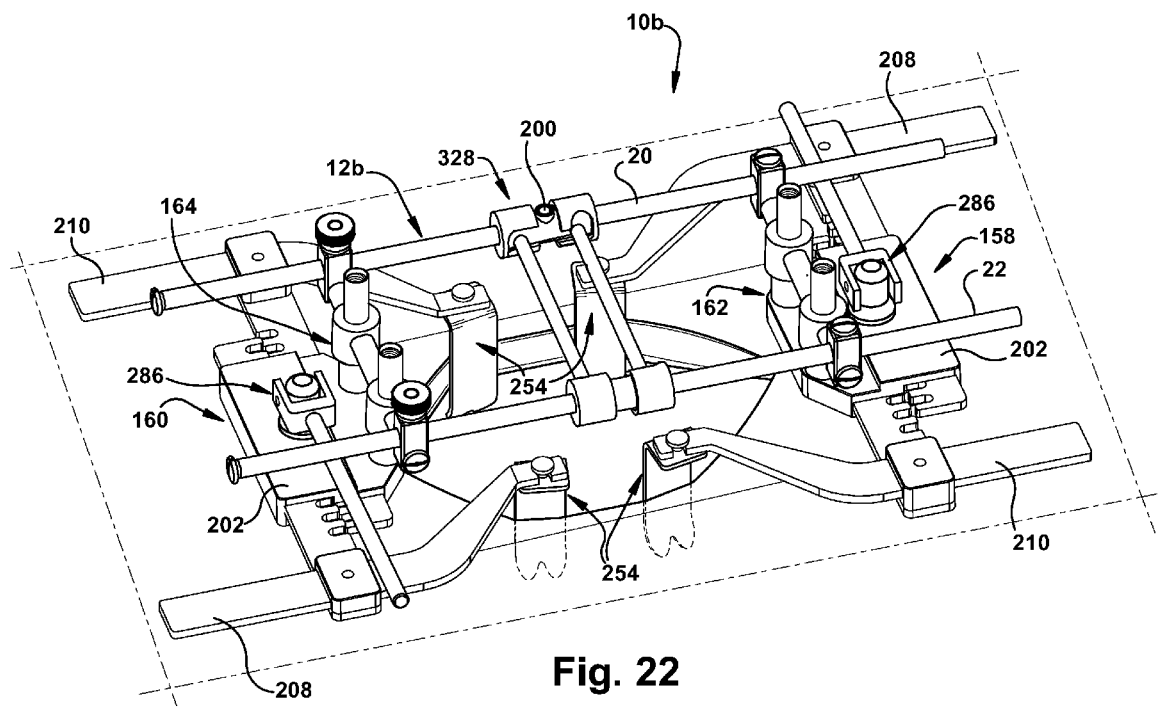
FIG. 22 is a perspective view showing a brace member and a gondola mounted to the first and second tissue retracting members in FIG. 21.

After spreading the tissue surrounding the spinal cord target, the spinal platform $10_b$ can be further assembled by mating the brace member $12_b$ with the first and second tissue retracting members 158 and 160 (FIG. 22). For example, the gondola 328 can be attached to the first and second longitudinal rails 20 and 22, whereafter the first and second longitudinal rails can then be attached to the first and second base members 162 and 164. The lateral position of the gondola 328 over the spinal cord target can be adjusted by sliding the gondola along the first and second longitudinal rails 20 and 22. Once the gondola 328 is suitably positioned over the spinal cord target, the first and second keeper members 354 and 356 can be mated with the first and second mating portions 338 and 340 to secure the gondola. Additionally, a screw 200 can be mated with the axial channel 352 of the first mating portion 338 to further secure the gondola 328.

Figure 23:
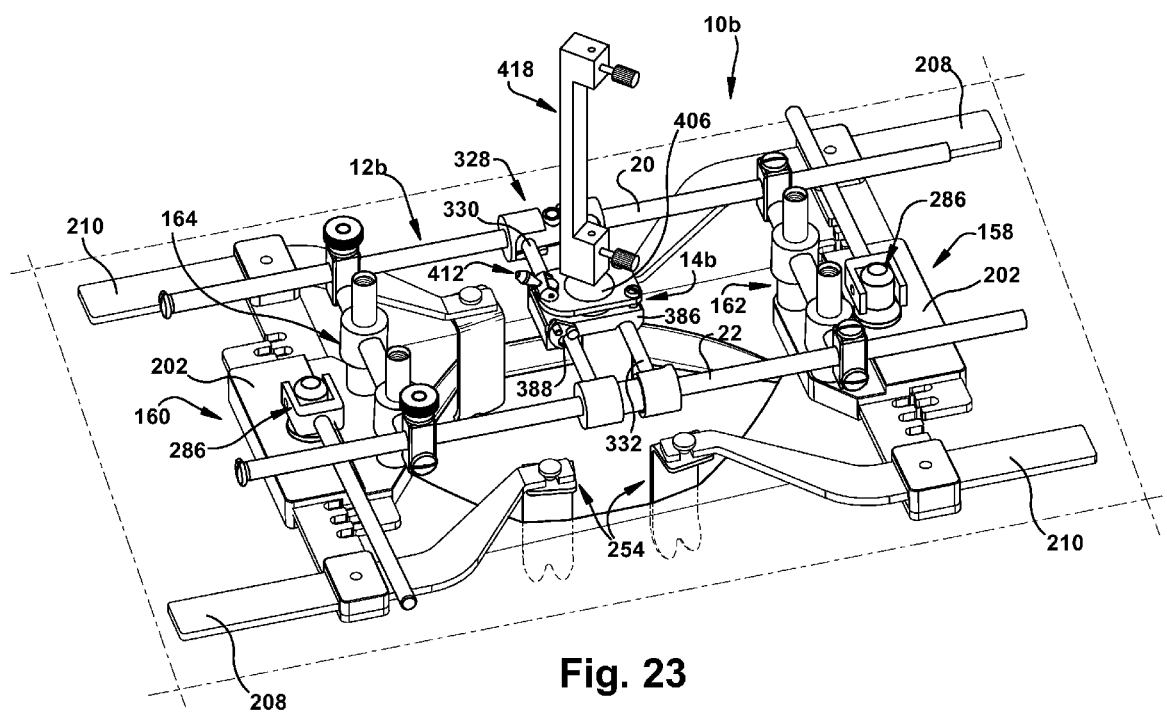
FIG. 23 is a perspective view showing the spinal platform of FIG. 13 securely mounted to the spinal column.

Once the gondola 328 is secured in place over the spinal cord target, the carriage member $14_b$ can be mated with the gondola by mating the first and second tracks 330 and 332 of the gondola with the first and second tracks 386 and 388 of the carriage member, respectively (FIG. 23). After appropriately positioning the carriage member 14$_b$ over the spinal cord target, the first and second locking mechanisms 100 and 102 can be operated by tactile force to engage the second track 332 of the gondola 328 and thereby securely position the carriage member over the spinal cord target. Next, the spherical member 406 can be seated in the bowl-shaped channel 88 of the lower block 368 and secured therein by mating the clamp plate 392 with the lower block. As shown in FIG. 23, a guide member 418 for securing the surgical instrument can then be operably attached to a tubular member 408 of the spherical member 406. After the guide member 418 has been secured to the spherical member 406, a surgical instrument (not shown), such as the cannula disclosed in U.S. Provisional Patent Application Ser. No. 61/078,004, filed Jul. 3, 2008, the entirety of which is hereby incorporated by reference, can be mated with the guide member and the spherical member.

At Step 150$_c$, the spherical member 406 can be manipulated to adjust the coronal or sagittal angle of the surgical instrument. For example, the spherical member 406 can be rotated in a desired x and/or y dimension until the surgical instrument obtains the desired coronal or sagittal angle. Once the desired coronal or sagittal angle is obtained, the universal joint locking mechanism 412 can be operated to stabilize the spherical member 406 in the bowl-shaped channel 88 of the carriage member 14$_b$ and thereby secure the surgical instrument at the desired coronal or sagittal angle. The surgical instrument can then be urged through the channel 410 of spherical member 406 and advanced along a constrained trajectory to the spinal cord target.

It will be appreciated that a real-time imaging technique, such as OCT imaging can be used to assist in accurately delivering the surgical instrument to the spinal cord target. Additionally, it will be appreciated that the surgical instrument can include an electrode (not shown) to assist in placing the surgical instrument via micro-electric recording. To deliver the therapeutic agent to the ventral horn, a distal tip (not shown in detail) of the surgical instrument can be advanced through the marginal zone, the substantia gelatinosa, the body of the dorsal horn, and the intermediate horn of the spinal cord into a portion of the ventral horn.

Once the surgical instrument is securely positioned at the spinal cord target, a therapeutically effective amount of the therapeutic agent can be delivered to the spinal cord target at Step 154$_c$. For example, a therapeutically effective amount of fetal progenitor cells can be infused through the surgical instrument at an appropriate rate and concentration. The fetal progenitor cells may then be delivered to the ventral horn to mitigate or prevent symptoms associated with the motor neuron disease.

Following successful delivery of the therapeutic agent to the spinal cord target, the surgical instrument (along with the entire spinal platform 10$_b$) can be removed from the subject and the incision closed in four layers. For example, the dura mater can be closed with a running stitch (not shown), in a watertight fashion, using a 4-0 Nurolon suture. A strip of Gelfoam (not shown) can be placed over the closure. A 0 Vicryl suture (not shown) can then be used for the deep muscular layer, obliterating the dead space and reducing the potential for developing epidural hematoma. The second layer, the fascia, can also be closed with a 0 Vicryl suture (not shown) in a watertight fashion. Next, the dermal layer can be closed with 2-0 Vicryl sutures (not shown) followed by skin stapling.

It will be appreciated that the spinal platform 10$_b$ can also be used to deliver a therapeutic agent to a cervical spinal cord target via a method similar to the one described above. Where the spinal cord target is located between C3 and C4, for example, an incision can be made to expose the vertebrae. After performing a laminectomy, the first and second tissue retracting members 158 and 160 and the brace member 12$_b$ can be attached between C3 and the occipital bone. For example, the first tissue retracting member 158 can be attached to the lamina or pedicle of C3 and then actuated to spread the tissue surrounding the spinal cord target (as described above). The first and second base members 162 and 164 can then be secured to the first tissue retracting member 158 and the occipital bone, respectively, via a plurality of self-tapping screws 310.

After the first and second base members 162 and 164 have been securely attached to C3 and the occipital bone, respectively, the other components of the spinal platform 10$_b$ can be assembled as described above. Once the spinal platform 10$_b$ is assembled, a surgical instrument (e.g., a cannula) can be used to deliver a therapeutic agent to the spinal cord target (as described above). Advantageously, the low profile and stabilized configuration of the spinal platform 10$_b$ facilitates delivery of the therapeutic agent to a cervical portion of the spinal cord.

It will also be appreciated that the method 144$_c$ can be performed without surgically exposing the spinal cord target. For example, a minimally invasive, stereotactic version of the method 144$_c$ can be performed using an MRI scanner. Such an approach would not require that an incision be made about the spinal cord target. Rather, a minimally invasive, stereotactic version the method 144$_c$ would permit a surgical instrument to be driven through the skin and muscles surrounding the spinal cord directly to the spinal cord target.

From the above description of the invention, those skilled in the art will perceive improvements, changes and modifications. For example, it will be appreciated that assembly of the spinal platform 10, 10$_a$, and 10$_b$, as well as the delivery of the therapeutic agent to the spinal cord target, is not limited to the sequential order of steps described above. Such improvements, changes, and modifications are within the skill of the art and are intended to be covered by the appended claims.

Having described the invention, we claim:

1. A spinal platform for delivering a therapeutic agent to a spinal cord target, said spinal platform comprising:

a brace member for attachment to a plurality of bony structures surrounding at least a portion of the spinal cord target, said brace member comprising oppositely disposed first and second longitudinal rails and a plurality of attachment members operably connected to and extending between said first and second longitudinal rails, said plurality of attachment members for securing said brace member to the plurality of bony structures, each of said first and second longitudinal rails including a proximal end portion, a distal end portion, and a middle portion extending between said proximal and distal end portions;

a carriage member operatively coupled to and movable along said brace member; and a universal joint for adjusting the coronal or sagittal angle of a surgical instrument, said universal joint being seated within a portion of said carriage member and being capable of delivering the therapeutic agent to the spinal cord target;

wherein said plurality of attachment members further comprises:

a first base member operably secured to said proximal end portion of each of said first and second longitudinal rails; and a second base member operably secured to said distal end portion of each of said first and second longitudinal rails;
wherein each of said first and second base members comprises a cross bar, said cross bar comprising first and second screw mounts integrally formed with and situated between a rod-shaped center section, a first rod-shaped outer section, and a second rod-shaped outer section.

2. The spinal platform of claim 1, wherein said plurality of attachment members further comprises:
first clamp member operably secured to said proximal end portion of each of said first and second longitudinal rails; and
a second clamp member operably secured to said distal end portion of each of said first and second longitudinal rails.

3. The spinal platform of claim 1, wherein each of said first and second clamp members comprises:
a T-shaped clamp body, said clamp body comprising a receptacle portion and an arm portion extending radially from said receptacle portion, said receptacle portion including first and second openings for receiving said first and second longitudinal rails, respectively, said arm portion including an axially-extending channel;
an L-shaped clamp pin having a first end and a contacting portion, said first end for insertion into said axially-extending channel; and
a clamp fastener for mating with said first end of said clamp pin to secure said clamp pin to said receptacle portion.

4. The spinal platform of claim 1 further comprising:
first and second pivot members for securing said first base member to said first and second longitudinal rails, said first pivot member including separate channels for receiving said second longitudinal rail and said first outer section of said first base member, said second pivot member including separate channels for receiving said first longitudinal rail and said second outer section of said first base member; and
third and fourth pivot members for securing said second base member to said first and second longitudinal rails, said third pivot member including separate channels for receiving said second longitudinal rail and said first outer section of said second base member, said fourth pivot member including separate channels for receiving said first longitudinal rail and said second outer section of said second base member.

5. The spinal platform of claim 1 further comprising:
a micromanipulator operably coupled to said carriage member, said micromanipulator for guiding the surgical instrument along a constrained trajectory; and
a pump operably connected to said micromanipulator, said pump for delivering the therapeutic agent to the surgical instrument.

6. The spinal platform of claim 1 further comprising:
a first tissue retracting member operably connected to said first base member; and
a second tissue retracting member operably connected to said second base member;
wherein each of said first and second tissue retracting members comprises opposable first and second retracting arms having a distal end portion and a proximal end portion, said distal end portion of each of said first and second retracting arms including a removable tissue retractor blade extending axially therefrom.

7. The spinal platform of claim 1, wherein said carriage member further comprises:

a main body having oppositely disposed first and second major surfaces, said second major surface including oppositely disposed first and second tracks;
a bowl-shaped channel extending between said first and second major surfaces; and
a plurality of oppositely disposed locking mechanisms attached to said main body.

8. The spinal platform of claim 1, wherein said brace member further comprises:
a gondola slidably mounted to and axially situated between said first and second longitudinal rails of said brace member, said gondola comprising first and second parallel tracks, each of said first and second parallel tracks having first and second ends integrally formed with a first cylindrical mating portion and a second cylindrical mating portions, each of said first and second cylindrical mating portions including a groove for receiving said first and second longitudinal rails, respectively.

9. The spinal platform of claim 8, wherein said gondola is slidably mounted to said carriage member so that a first track and a second tracks of said carriage member are mated with said first and second parallel tracks of said gondola, respectively.

10. The spinal platform of claim 1, said universal joint further comprising:
a spherical member including oppositely disposed tubular members integrally formed with said spherical member, said spherical member including a channel that extends between said tubular members through said spherical member.

11. The spinal platform of claim 1, said universal joint further comprising:
an upper platform having oppositely disposed first and second major surfaces;
a bowl-shaped lower portion for mating with said carriage member, said lower portion being integrally formed with said second major surface of said upper portion; and
a channel extending from said first surface of said upper platform through said lower portion.

12. The spinal platform of claim 1, wherein each of said first and second screw mounts includes a channel for receiving a percutaneous post.

13. The spinal platform of claim 12, wherein said percutaneous post has an elongated, cylindrical configuration and a length defined by a proximal end portion, a distal end portion, and a middle portion extending between said proximal and distal end portions, said percutaneous post further including a threaded inner bore that is adapted to receive a self-tapping screw.

14. The spinal platform of claim 13, wherein said self-tapping screw includes a proximal end portion, a distal end portion, and a middle portion extending between said proximal and distal end portions, said proximal end portion including a mating portion and a tapered threaded portion that is integrally formed with said mating portion and adapted to mate with said threaded inner bore of said percutaneous post, said distal end portion including a pointed end and a plurality of threads for boring into a bony structure.

15. A spinal platform for delivering a therapeutic agent to a spinal cord target, said spinal platform comprising:
a brace member for attachment to a plurality of bony structures surrounding at least a portion of the spinal cord target, said brace member comprising oppositely disposed first and second longitudinal rails and first and second base members for securing said brace member to the plurality of bony structures, each of said first and second longitudinal rails including a proximal end portion and a distal end portion, said first base member being operably secured to said proximal end portion of each of said first and second longitudinal rails, and said second base member being operably secured to said distal end portion of each of said first and second longitudinal rails;

wherein each of said first and second base members comprises a cross bar, said cross bar comprising first and second screw mounts integrally formed with and situated between a rod-shaped center section, a first rod-shaped outer section, and a second rod-shaped outer section;

a first tissue retracting member operably connected to said first base member;

a second tissue retracting member operably connected to said second base member;

wherein each of said first and second tissue retracting members comprises opposable first and second retracting arms having a distal end portion and a proximal end portion, said distal end portion of each of said first and second retracting arms including a removable tissue retractor blade extending axially therefrom;

a carriage member operatively coupled to and movable along said brace member; and a universal joint for adjusting the coronal or sagittal angle of a surgical instrument, said universal joint being seated within a portion of said carriage member and being capable of delivering the therapeutic agent to the spinal cord target.

* * * * *